US009001408B2

(12) United States Patent
Yamada et al.

(10) Patent No.: US 9,001,408 B2
(45) Date of Patent: Apr. 7, 2015

(54) ELECTROCHROMIC DEVICE

(75) Inventors: Kenji Yamada, Yokohama (JP); Shinjiro Okada, Kamakura (JP); Kazuya Miyazaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 130 days.

(21) Appl. No.: 13/449,150

(22) Filed: Apr. 17, 2012

(65) Prior Publication Data
US 2012/0314272 A1 Dec. 13, 2012

Related U.S. Application Data

(63) Continuation of application No. PCT/JP2011/080201, filed on Dec. 27, 2011.

(30) Foreign Application Priority Data

Jun. 7, 2011 (JP) .................................. 2011-127678
Sep. 22, 2011 (JP) .................................. 2011-206999

(51) Int. Cl.
*G02F 1/15* (2006.01)
*C07D 495/14* (2006.01)
(Continued)

(52) U.S. Cl.
CPC ............... *G02F 1/15* (2013.01); *C07D 495/14* (2013.01); *C07D 333/16* (2013.01); *C07D 333/32* (2013.01); *C07D 409/04* (2013.01);
(Continued)

(58) Field of Classification Search
USPC .............. 359/265–275; 345/49, 105; 514/648
See application file for complete search history.

(56) References Cited

U.S. PATENT DOCUMENTS 7,746,533 B2 *  6/2010  Sotzing et al. ................. 359/265
2002/0141032 A1  10/2002  Guarr
(Continued)

FOREIGN PATENT DOCUMENTS

CN    101432250 A    5/2009
CN    103124732 A    5/2013
(Continued)

OTHER PUBLICATIONS

Yanming Sun, Yongqiang Ma, et al., Advanced Functional Materials 2006, 16, pp. 426-432, "High-Performance and Stable Organic Thin-Film Transistors Based on Fused Thiophenes".
(Continued)

*Primary Examiner* — Tuyen Tra
(74) *Attorney, Agent, or Firm* — Canon U.S.A. Inc., IP Division

(57) ABSTRACT

There is provided an EC device having stability against redox reaction cycles, high transparency, i.e., the EC device does not absorb light in the visible region in a bleached state, and having excellent response speed. The electrochromic device includes a pair of electrodes and a composition arranged between the pair of electrodes, the composition containing an electrolyte and an organic electrochromic compound, in which the organic electrochromic compound includes an electrochromic portion that exhibits electrochromic properties and an aromatic ring directly bonded to the electrochromic portion, the electrochromic portion forms one conjugated plane, an atom of the aromatic ring and adjacent to an atom bonded to the electrochromic portion has a substituent having a volume equal to or larger than the volume of a methyl group, and a cathodically electrochromic organic compound is further contained in addition to the organic electrochromic compound.

14 Claims, 4 Drawing Sheets

(51) Int. Cl.

| | |
|---|---|
| *C07D 333/16* | (2006.01) |
| *C07D 333/32* | (2006.01) |
| *C07D 409/04* | (2006.01) |
| *C07D 491/056* | (2006.01) |
| *C07D 495/04* | (2006.01) |
| *C07D 277/56* | (2006.01) |
| *C07F 7/08* | (2006.01) |

(52) U.S. Cl.
CPC .......... *C07D491/056* (2013.01); *C07D 495/04* (2013.01); *C07D 277/56* (2013.01); *C07F 7/0816* (2013.01); *G02F 1/1521* (2013.01)

(56) References Cited

U.S. PATENT DOCUMENTS

| | | |
|---|---|---|
| 2012/0314272 A1 | 12/2012 | Yamada |
| 2013/0100517 A1 | 4/2013 | Yamada |
| 2013/0190513 A1 | 7/2013 | Yamada et al. |

FOREIGN PATENT DOCUMENTS

| | | |
|---|---|---|
| JP | 51-146253 A | 12/1976 |
| JP | 56-067881 A | 6/1981 |
| JP | 2006-089413 A | 4/2006 |
| JP | 2007-241238 A | 9/2007 |
| JP | 2007-291013 A | 11/2007 |
| JP | 2008-512727 A | 4/2008 |
| JP | 2008-116665 A | 5/2008 |
| JP | 2008-207170 A | 9/2008 |
| JP | 2008-248249 A | 10/2008 |
| JP | 2009-215333 A | 9/2009 |
| JP | 2009-260287 A | 11/2009 |
| JP | 2010-117409 A | 5/2010 |
| WO | 2006/029344 A2 | 3/2006 |
| WO | 2010/013532 A1 | 2/2010 |
| WO | 2012/002185 A1 | 1/2012 |

OTHER PUBLICATIONS

Christian B. Nielsen et al. "Discrete Photopatternable [pi]-Conjugated Oligomers for Electrochromic Devices", Journal of the American Chemical Society, vol. 130, No. 30, Jul. 1, 2008, pp. 9734-9746, XP055142908.

Zhang, et al., "Synthesis, Self-Assembly and Solution-Processed Field-Effect Transistors of a Liquid Crystalline Bis (dithienothiophene) Derivative", J. Phys. Chem. C, (2009), pp. 16232-16237, vol. 113.

Zhang, et al., "Effect of substituents on electronic properties, thin film structure and device performance of dithienothiophene-phenylene cooligomers", Thin Solid Films, (2009), pp. 2968-2973, vol. 517.

Wang, et al., Nanopatterning of Donor/Acceptor Hybrid Supramolecular Architectures on Highly Oriented Pyrolytic Graphite: A Scanning Tunneling Microscopy Study, J. Am. Chem. Soc., (2008), pp. 13433-13441, vol. 130.

\* cited by examiner

ELECTROCHROMIC DEVICE

CROSS-REFERENCE TO RELATED APPLICATIONS

This application is a Continuation of International Patent Application No. PCT/JP2011/080201, filed Dec. 27, 2011, which claims the benefit of Japanese Patent Application No. 2011-127678 filed Jun. 7, 2011 and No. 2011-206999 filed Sep. 22, 2011, which are hereby incorporated by reference herein in their entirety.

TECHNICAL FIELD

The present invention relates to a novel electrochromic device.

BACKGROUND ART

There has been active development of electrochromic (hereinafter, also abbreviated as "EC") devices including electrochromic materials in which optical absorption properties, such as colored states and optical transmittances of materials, are changed by electrochemical redox reactions.

PTL 1 discloses an EC device in which a conductive polymer is formed on a transparent electrode and in which an electrolytic solution is enclosed between the electrode and a counter electrode. PTL 2 discloses a solution-phase EC device in which an electrolytic solution containing a low-molecular-weight molecule, such as viologen, dissolved therein is enclosed between a pair of electrodes.

For the conductive polymer described in PTL 1, an EC layer can be directly formed on the electrode by the electrolytic polymerization of a monomer. Known examples of the conductive polymer that forms the EC layer include polythiophene, polyaniline, and polypyrrole.

In the case where such a conductive polymer is electrochemically oxidized or reduced, the π-conjugated chain length of a main chain is changed, thereby changing the electron state of the highest occupied molecular orbital (HOMO). Thus, a wavelength absorbed by the conductive polymer is changed.

These conductive polymers absorb light in the visible region in the electrically neutral state and thus are colored. Oxidation of these conductive polymers allows wavelengths absorbed by the conductive polymers to shift to longer wavelengths.

In the case of the shift of the wavelengths to the infrared region, the polymers do not exhibit absorption in the visible region, so that the EC device is bleached.

Meanwhile, for the EC material containing the viologen-based compound described in PTL 2, dications are dissolved in the solution in a bleached state. Viologen is converted into radical cations by a reduction reaction, precipitated on the electrode, and colored.

CITATION LIST

Patent Literature

PTL 1 Japanese Patent Laid-Open No. 56-67881
PTL 2 Japanese Patent Laid-Open No. 51-146253

Non Patent Literature

NPL 1 Advanced Functional Materials, 16, 426 (2006)

In PTL 1, the delocalization of unstable radical cations in its molecule enhances stability. However, the stability is not sufficient. In the case where the redox reaction is repeated, the material is degraded, thereby disadvantageously reducing the performance of the EC device.

Furthermore, the conductive polymer absorbs visible light in the electrically neutral state. That is, the polymer is colored in the electrically neutral state. Thus, if there is a portion where the electrochemical reaction occurs insufficiently, the portion is maintained to be a colored state, thus causing difficulty in achieving high transparency.

In the viologen-based organic EC compound described in PTL 2, the repetition of the precipitation and dissolution causes degradation phenomena.

The degradation phenomena can be attributed to irreversible crystallization and insolubilization due to polymerization. The degradation leads to a "residual portion" in which the portion is not transparent even in a state in which the portion should be bleached.

Furthermore, the viologen-based organic EC compound forms unstable radical cations at the time of reduction. Unfortunately, the molecule does not have a mechanism for stabilizing the radical cations, so that the stability of the radical cations is low. Hence, the device has low durability.

Accordingly, it is an object of the present invention to provide an EC device having high durability, a high response speed, and high transparency when the device is bleached.

SUMMARY OF INVENTION

The present invention provides an electrochromic device including a pair of electrodes and a composition arranged between the pair of electrodes, the composition containing an electrolyte and an organic electrochromic compound, in which the organic electrochromic compound includes an electrochromic portion that exhibits electrochromic properties and an aromatic ring directly bonded to the electrochromic portion, the electrochromic portion forms one conjugated plane, an atom of the aromatic ring and adjacent to an atom bonded to the electrochromic portion has a substituent having a volume equal to or larger than the volume of a methyl group, and the pair of electrodes has an interelectrode distance of 150 µm or less.

Further features of the present invention will become apparent from the following description of exemplary embodiments with reference to the attached drawings.

DESCRIPTION OF EMBODIMENTS

An EC device according to the present invention includes a pair of electrodes and a composition arranged between the pair of electrodes, the composition containing an electrolyte and an organic electrochromic compound, in which the organic electrochromic compound includes an electrochromic portion that exhibits electrochromic properties and an aromatic ring directly bonded to the electrochromic portion, the electrochromic portion forms one conjugated plane, an atom of the aromatic ring and adjacent to an atom bonded to the electrochromic portion has a substituent having a volume equal to or larger than the volume of a methyl group, and the pair of electrodes has an interelectrode distance of 150 μm or less.

Figure 1:
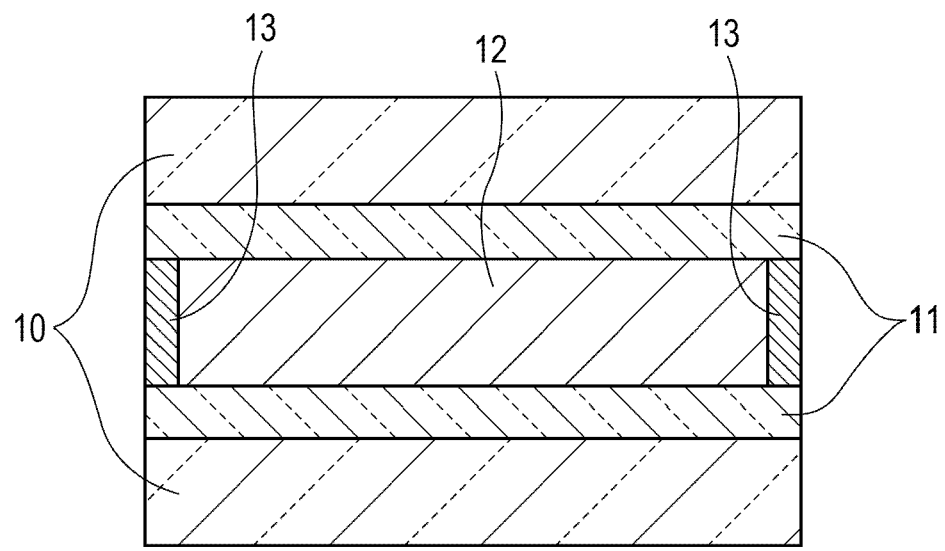
FIG. 1 is a schematic cross-sectional view of an EC device according to an embodiment of the present invention.

An EC device according to the present invention will be described below with reference to the drawings. FIG. 1 is a schematic cross-sectional view of an EC device according to an embodiment of the present invention.

The EC device illustrated in FIG. 1 includes a pair of transparent electrodes 11 and a composition 12 arranged between the pair of transparent electrodes, the composition 12 containing an electrolyte and an organic EC compound. The pair of the electrodes has a constant interelectrode distance defined by spacers 13.

In the EC device, the pair of the electrodes is arranged between a pair of transparent substrates 10.

The term "transparent" used here indicates that the light transmittance is 10% to 100% in the visible region. However, the EC device is merely an exemplary EC device according to the present invention. The EC device according to the present invention is not limited thereto.

For example, an antireflection coating film may be arranged between one of the transparent substrates 10 and a corresponding one of the transparent electrodes 11 and between one of the transparent electrodes 11 and the organic EC medium 12. The EC composition is a composition containing an organic EC compound. The EC composition is also merely referred to as a "liquid" or "composition".

The composition 12 contained in the EC device according to the present invention will now be described. The composition 12 is one in which the organic EC compound and a supporting electrolyte are dissolved in a solvent.

The organic EC compound according to this embodiment has an electrochromic portion and an aromatic ring-containing peripheral portion. The electrochromic portion is a portion that provides electrochromic properties. The peripheral portion has a substituent that protects the electrochromic portion.

In this embodiment, the aromatic ring in the organic EC compound and the substituent on the aromatic ring are collectively referred to as the "peripheral portion".

The peripheral portion is bonded to the electrochromic portion where a redox reaction occurs. Preferably, the peripheral portion does not inhibit the redox reaction. Thus, the peripheral portion preferably has a high redox potential.

The peripheral portion protects the electrochromic portion. Thus, the compound has high stability against oxidation.

The EC device according to the present invention includes the compound having high stability against oxidation and thus has high durability.

The substituent of the peripheral portion inhibits the approach of another molecule to the electrochromic portion by the effect of steric hindrance, and so is also referred to as a "sterically hindered group" because of its function.

The electrochromic portion which exhibits electrochromic properties and which has one conjugated plane has a structure including one or more heteroaromatic rings, such as thiophene, pyrrole, furan, pyridine, thiazole, and imidazole, or aromatic hydrocarbon rings, such as a benzene ring, these rings having π-electron conjugated systems.

Here, π electrons on one heteroaromatic ring or one aromatic ring are delocalized and distributed over the ring. Thus, one ring may be regarded as forming one conjugated plane.

Furthermore, also in a structure in which two or more heteroaromatic rings or aromatic rings are linked together, π electrons are delocalized on these rings. Thus, the rings may be regarded as forming one conjugated plane.

In the case where two or more heteroaromatic rings are linked together, higher coplanarity of the rings is preferred. This is because higher coplanarity results in the extension of molecular conjugation and longer molecular conjugation results in higher stability of the molecule.

However, in the EC device according to the present invention, when the organic EC compound is bleached, preferably, the organic EC compound does not absorb light in the visible region. Thus, preferably, the conjugated structure of the aromatic ring in the electrochromic portion is not excessively long.

The reason for this is that a long conjugates structure results in a narrow gap between the highest occupied molecular orbital (HOMO) and the lowest unoccupied molecular orbital (LUMO), thereby absorbing light in the visible region, which has low energy.

Note that each of the heteroaromatic ring and the aromatic hydrocarbon ring may have a substituent.

Examples of the substituent include an alkyl group, an aryl group, a heterocyclic group, an alkyl ether group, an alkoxy group, and an aralkyl group. In particular, examples of the substituent include an alkyl group having 1 to 10 carbon atoms, an alkoxy group having 1 to 10 carbon atoms, and a phenyl group.

The EC device according to the present invention contains a cathodically electrochromic organic compound. The cathodically electrochromic organic compound is an electrochromic compound that is colored when reduced.

In an EC device containing both the cathodically electrochromic organic compound and an anodically electrochromic organic compound, an electrochromic reaction occurs at each of a pair of electrodes, thus resulting in a rapid change in transmittance. That is, the EC device is one having a high speed of response.

Furthermore, the EC device according to the present invention may contain another compound.

While specific structural formulae of the electrochromic portion will be exemplified below, the electrochromic portion according to this embodiment is not limited thereto.

[Chem. 1]

W-1

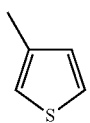

W-2

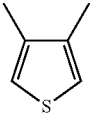

W-3

W-4 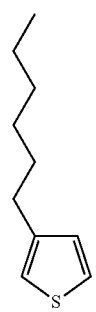
W-5 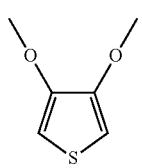
W-6 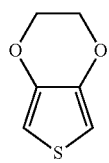
W-7 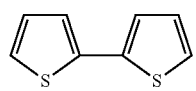
W-8 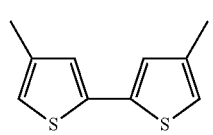
W-9 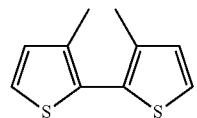
W-10 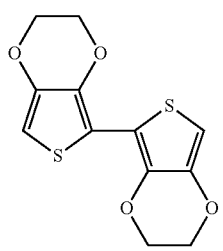
W-11 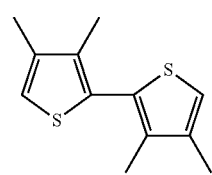
W-12 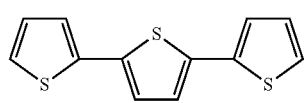
W-13 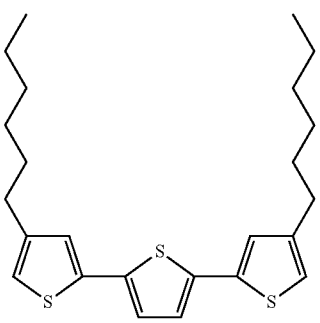
W-14 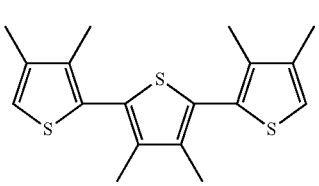
[Chem. 2]
W-15 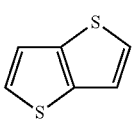
W-16 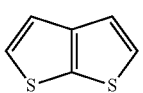
W-17 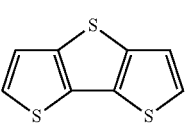
W-18 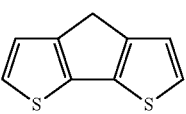
W-19 
W-20 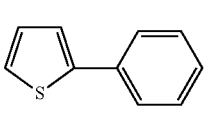
W-21 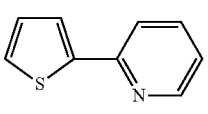

W-22

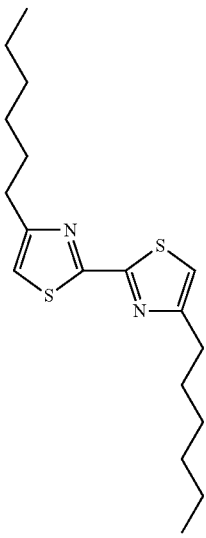

The electrochromic portion has a conjugated structure and thus has the effect of increasing the stability of radical cations formed in the molecule. A longer conjugated structure in the molecule enhances the effect. However, in order to provide a bleached state when the compound is in an electrically neutral state, preferably, the conjugated structure is not excessively long.

To increase the stability of radical cations, the possibility that the radical cations come into contact with other molecules may be reduced. For example, the presence of the peripheral portion included in the organic EC compound according to this embodiment may reduce the possibility that the radical cations come into contact with other molecules.

That is, the organic EC compound according to this embodiment includes the peripheral portion, so that the stability of radical cations is high even in the case of a molecule having a short conjugated structure.

It is conceivable that the instability of radical cations is attributed to the recombination of radicals and the abstraction of hydrogen from other molecules by radicals on the basis of the high reactivity of radicals.

That is, the reaction is caused by the contact of radicals with other molecules. It is thus conceivable that the suppression of the possibility of the contact with other molecules is highly effective.

Hence, the steric hindrance of a substituent on the aromatic ring and on an atom adjacent to an atom directly bonded to the electrochromic portion stabilizes radical cations. This is because the steric hindrance of the substituent inhibits the contact of radical cations with other molecules.

Examples of the aromatic ring contained in the peripheral portion include nitrogen atom-containing heteroaromatic rings, such as a pyridine ring and a pyrazine ring, in addition to a benzene ring and a naphthyl ring. Among them, an aromatic ring consisting of carbon atoms is preferred.

The substituent on the aromatic ring serves to allow the conjugated plane of the electrochromic portion to be orthogonalized to the plane of the peripheral portion and serves to protect the electrochromic portion where radical cations are formed on the basis of the effect of steric hindrance. From this point of view, a substituent having a volume equal to or larger than the volume of a methyl group is preferred.

This is because the peripheral portion having a substituent with a volume equal to or larger than the volume of a methyl group has a large excluded volume.

The term "excluded volume" used in this embodiment indicates the volume of a body of revolution defined by a locus formed by revolving the peripheral portion. In the body of revolution defined by a locus obtained by revolving the peripheral portion, a single bond that links the peripheral portion with the electrochromic portion serves as the axis of revolution.

Examples of the substituent having a volume equal to or larger than the volume of a methyl group according to this embodiment include alkyl groups, such as methyl, ethyl, isopropyl, tert-butyl, dodecyl, and cyclohexyl groups; aryl groups, such as phenyl and biphenyl groups, which may have a substituent; alkoxy groups, such as methoxy, isopropoxy, n-butoxy, and tert-butoxy groups; and alkyl ester groups, such as methyl ester, isopropyl ester, and tert-butyl ester groups.

As the substituent in the peripheral portion according to this embodiment, an electron-donating group, for example, an amino group or a diphenylamino group, having strong electron-donating properties may be used in addition to a substituent consisting of carbon, oxygen, and hydrogen.

Furthermore, an electron-withdrawing group, such as a halogen-containing group, e.g., a trifluoromethyl group, and a nitrile group, may be used. In particular, when the electrochromic portion is electron rich, an electron-withdrawing peripheral portion is effective.

Among them, in particular, electron-donating groups, such as alkyl groups and alkoxy groups, are preferred. Alkyl groups and alkoxy groups each having 1 to 10 carbon atoms may be preferably used.

In the case where an electron-donating group is contained, the electrochromic portion has a high electron density and thus has a low oxidation potential, thereby providing a device having a low driving voltage.

The peripheral portion according to this embodiment is a portion to which molecular conjugation in the electrochromic portion does not extend. The boundary between the electrochromic portion and the peripheral portion is determined by whether molecular conjugation is present or not.

In an actual molecule, however, fluctuations due to thermal motion and quantum-chemical fluctuations exist; hence, the molecular orbital is not completely disrupted. In this embodiment, in the case of small resonance, molecular conjugation is regarded as not being present.

A smaller resonance between the electrochromic portion and the peripheral portion is preferred. Thus, π-electron orbitals of the electrochromic portion and the peripheral portion preferably intersect at an angle close to 90°. In the case where the π-electron orbitals of the peripheral portion and the electrochromic portion are orthogonalized, the resonance is extremely small.

Preferably, two atoms adjacent to an atom having a bond that links the electrochromic portion and the peripheral portion each have a substituent having a volume equal to or larger than the volume of a methyl group in order that the angle between the electrochromic portion and the peripheral portion may be close to 90°.

Furthermore, preferably, the oxidation potential of the peripheral portion is relatively higher than that of the electrochromic portion. That is, an organic EC compound having the peripheral portion that is less likely to be oxidized is more preferred. The fact that the redox potential is high is that the HOMO lies deep.

The dihedral angle formed by the electrochromic portion and the peripheral portion according to this embodiment is preferably close to 90°. The reason for this is that because a molecule having a conjugated structure has high planarity, a reaction with another molecule occurs in the direction perpendicular to the conjugated plane.

The following table illustrates, as an example, a value of the dihedral angle between a dithienothiophene ring and a phenyl ring determined by molecular orbital calculation. The dithienothiophene ring is illustrated as exemplified structure W-17 described above. Note that dithienothiophene corresponds to the electrochromic portion and that a phenyl group substituted with hydrogen or a methyl group corresponds to the peripheral portion.

The dihedral angle in a ground state was determined by structural optimization calculations using Gaussian 03* Revision D. 01. The density functional theory was used as a quantum chemical calculation method using the B3LYP functional.

In Gaussian 03, Revision D. 01, the 6-31G* basis function was used.

*Gaussian 03, Revision D. 01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004.

The fact that the HOMO of the electrochromic portion lies higher than the HOMO of the peripheral portion indicates that the electrochromic portion is likely to be oxidized compared with the peripheral portion.

Here, the fact that the HOMO lies high indicates that it lies closer to the vacuum level. Thus, the HOMO may also be expressed as the shallow HOMO.

Table 2 illustrates examples of a combination in which the electrochromic portion is more easily oxidized than the peripheral portion and illustrates molecular orbital calculation results of a single molecular structure that includes dithienothiophene serving as the electrochromic portion and a corresponding one of aromatic rings substituted with various substituents, each aromatic ring serving as the peripheral portion.

The molecular orbital calculations were conducted using the foregoing electronic state calculation software, Gaussian 03* Revision D. 01.

The calculated values from the molecular orbital calculations of the electrochromic portion were obtained on the assumption that the electrochromic portion is present in the form of an independent compound. The calculated values from the molecular orbital calculations of the peripheral portion were also obtained on the assumption that the peripheral portion is present not in the form of a substituent but in the form of an independent compound.

In the organic EC compound according to this embodiment, the molecular conjugation is broken between the electrochromic portion and the peripheral portion. Thus, characteristics of the entire molecule may be discussed by the foregoing calculation method.

In the case where dithienothiophene is used as the electrochromic portion and where the structures illustrated in the table are each used as the peripheral portion, the electrochromic portion has a higher HOMO energy than those of the peripheral portions. This structure is one in which the electrochromic portion is more likely to be oxidized.

TABLE 1

| Compound | (structure with dithienothiophene-phenyl, H substituents) | (structure with dithienothiophene-phenyl, H₃C substituents) |
|---|---|---|
| Dihedral angle between two rings | 28° | 90° |

As illustrated above, in the case where each of the atoms of the peripheral portion and adjacent to the atom bonded to the electrochromic portion has a substituent, the conjugated plane of the electrochromic portion intersects with the plane of the peripheral portion at an angle close to 90°, which is preferred.

It is well known that the oxidation potential of a molecular species correlates with the HOMO. A higher HOMO results in a lower oxidation potential. That is, in the organic EC compound according to this embodiment, the HOMO of the electrochromic portion lies preferably higher than the HOMO of the peripheral portion.

TABLE 2

| | | eV HOMO | eV LUMO |
|---|---|---|---|
| Peripheral portion | 4,4'-Di-tert-butyl-1,1-biphenyl group (peripheral portion of exemplified compound A-10) | −5.74 | −0.48 |
| | Terphenyl group (peripheral portion of exemplified compound A-7) | −5.97 | −0.74 |
| | Trimethylphenyl group (peripheral portion of exemplified compound A-1) | −6.20 | −0.36 |

TABLE 2-continued

| | | eV HOMO | eV LUMO |
|---|---|---|---|
| | 2-Isopropoxy-6-methoxyphenyl group (peripheral portion of exemplified compound A-11) | −5.67 | −0.36 |
| Electrochromic portion | Dithienothiophene | −5.63 | −0.93 |

While examples of the specific structural formula of the organic EC compound including the electrochromic portion and the peripheral portion according to this embodiment will be illustrated below, the organic EC compound according to the present invention is not limited thereto.

[Chem. 3]

A-1
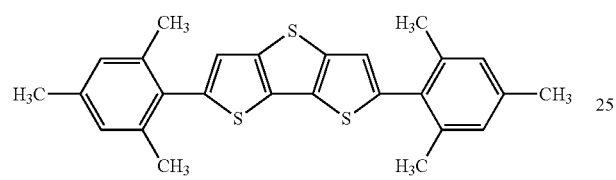

A-2
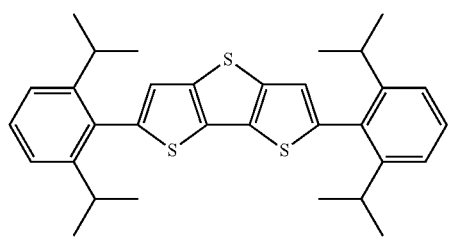

A-3
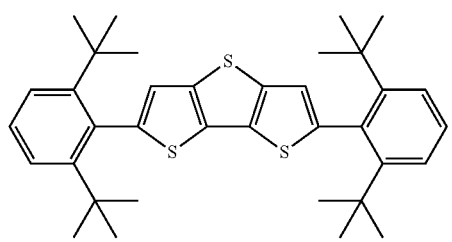

A-4
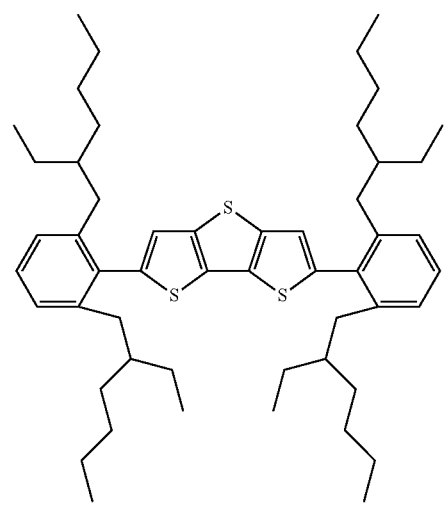

A-5
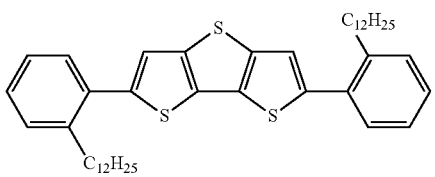

A-6
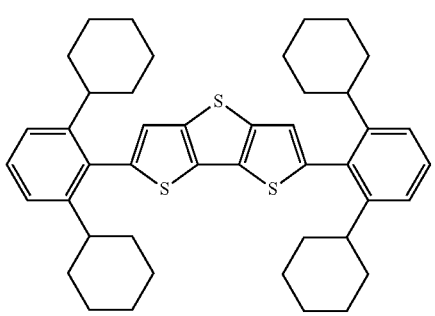

[Chem.4]

A-7
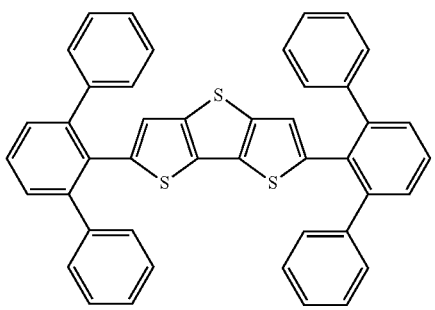

A-8
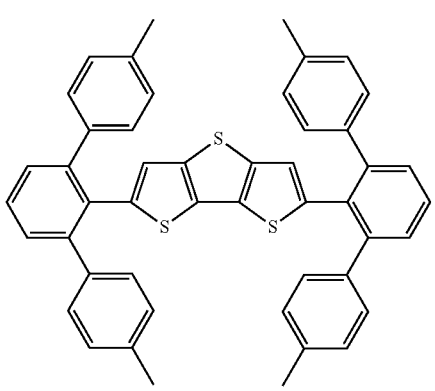

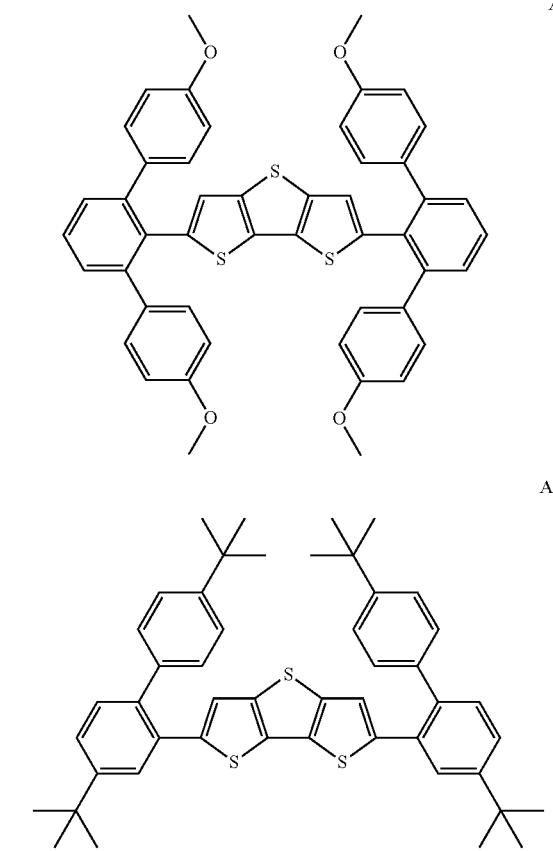
A-9
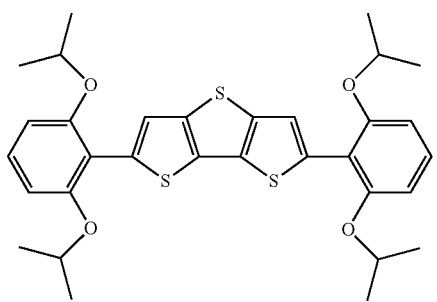
A-10
[Chem. 5]
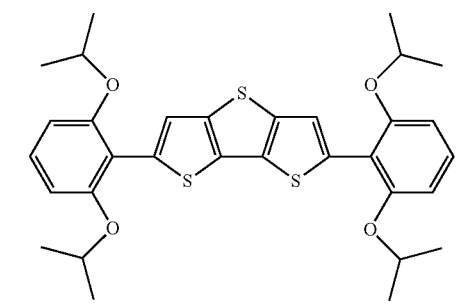
A-11
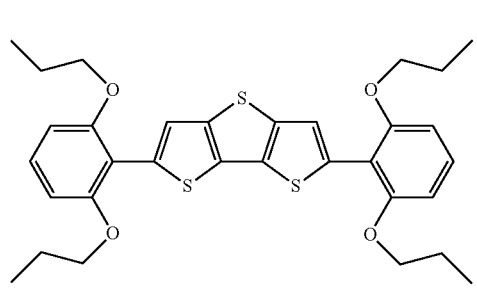
A-12
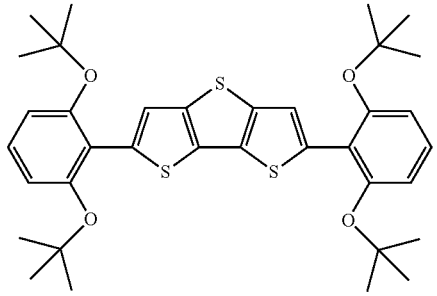
A-13
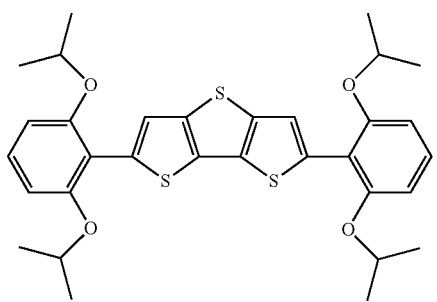
A-14
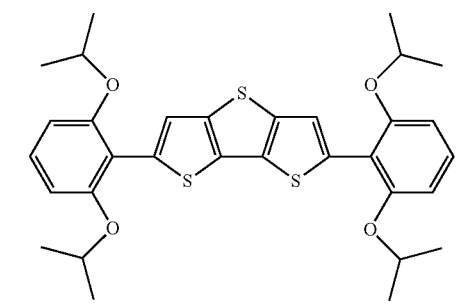
A-15
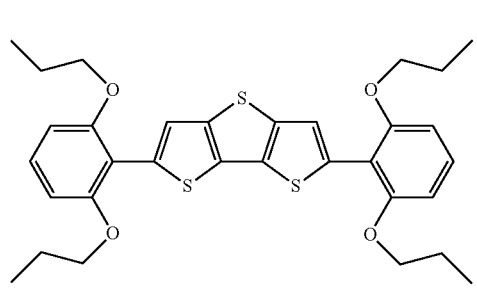
A-16
[Chem. 6]
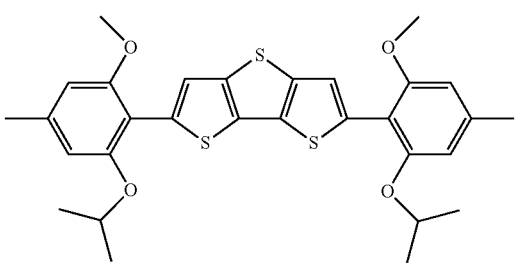
A-17
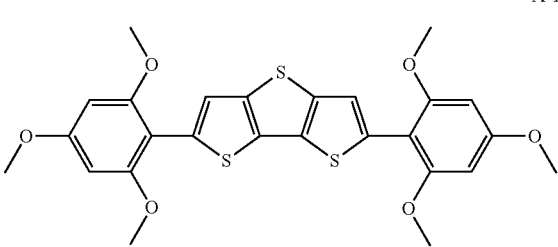
A-18

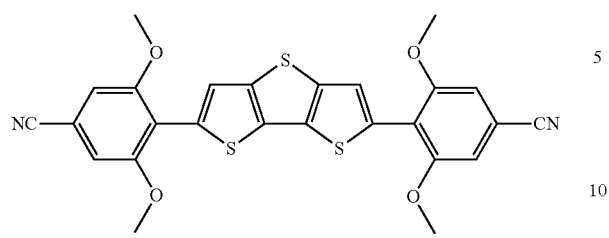
A-19
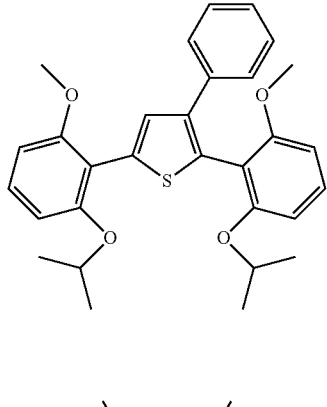
B-4
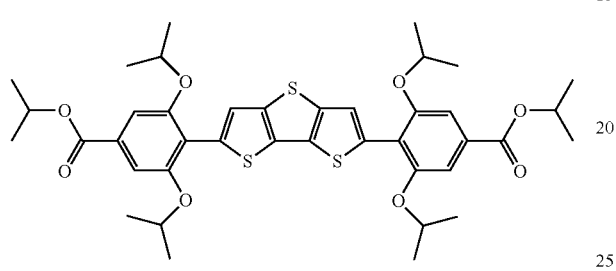
A-20
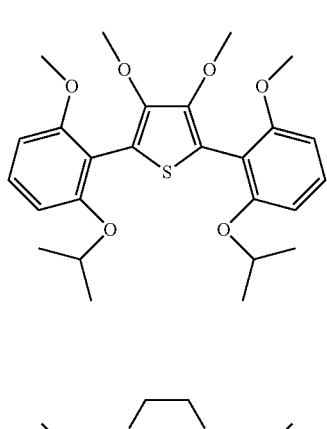
B-5
[Chem. 7]
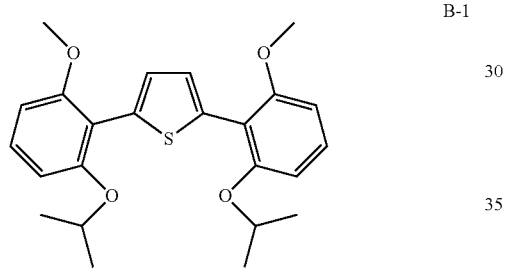
B-1
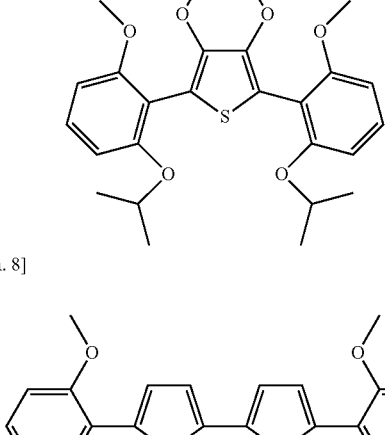
B-6
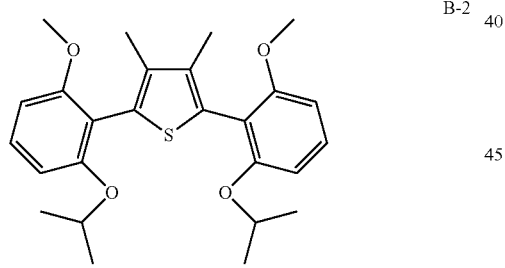
B-2
[Chem. 8]
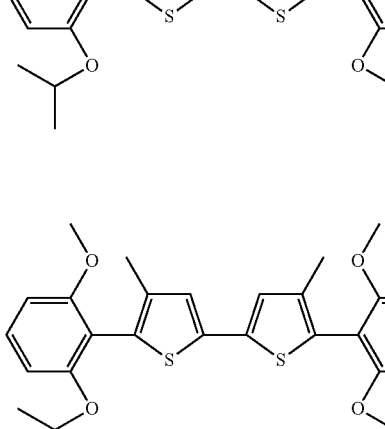
B-7
B-3
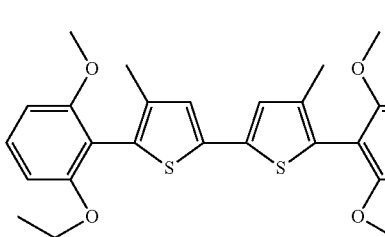
B-8

B-9
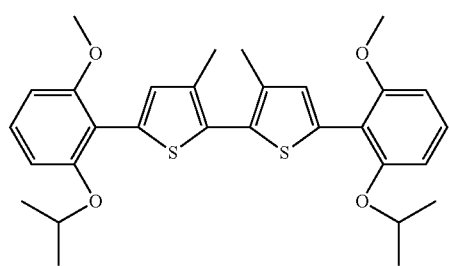
B-10
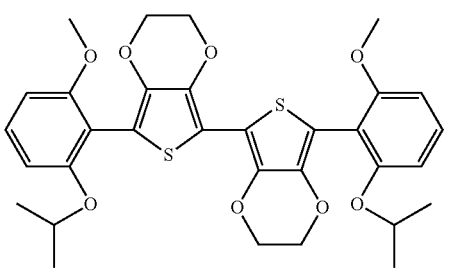
B-11
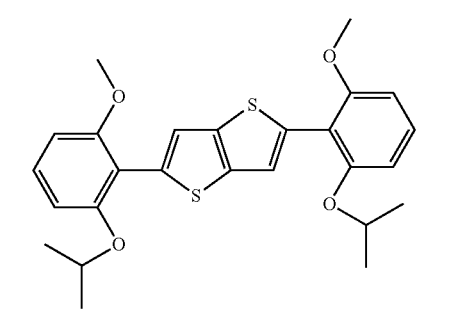
B-12
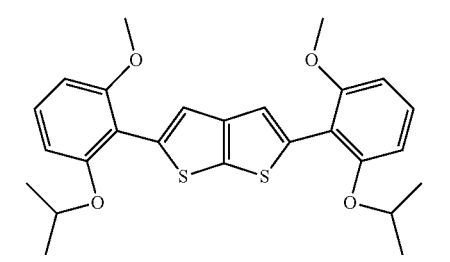
[Chem. 9]
B-13
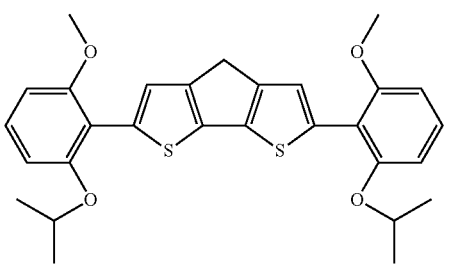
B-14
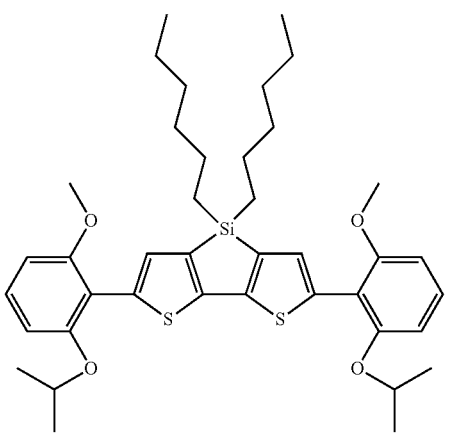
B-15
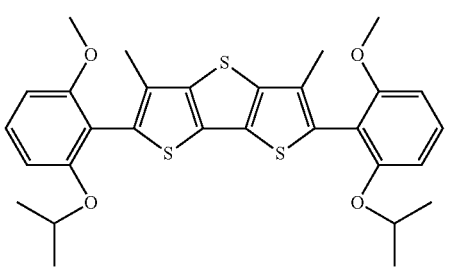
B-16
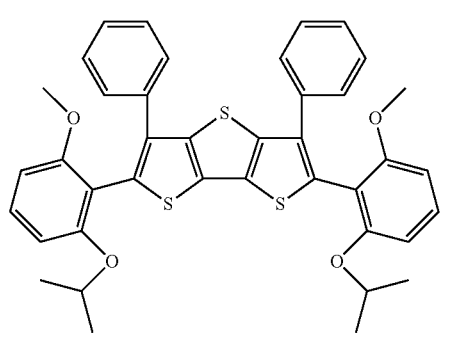
B-17
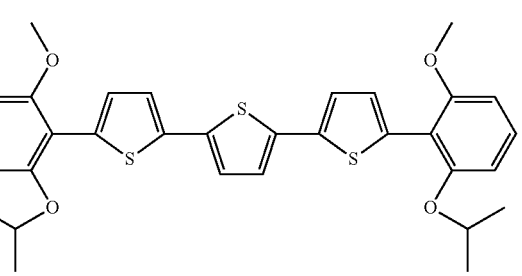

-continued

B-18
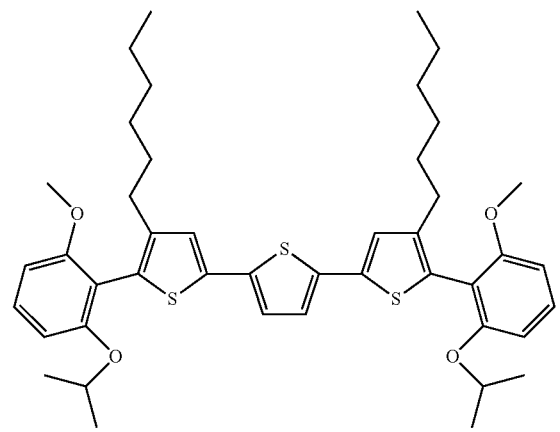

[Chem. 10]

B-19
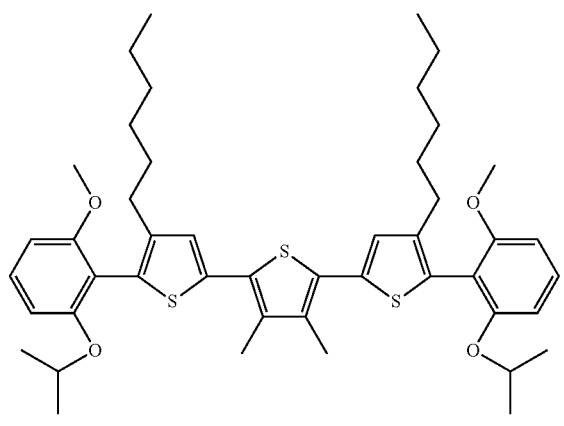

B-20
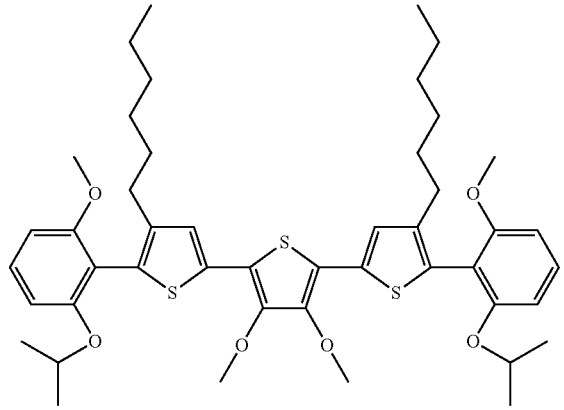

B-21
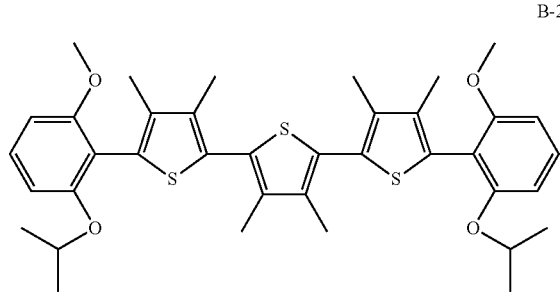

-continued

B-22
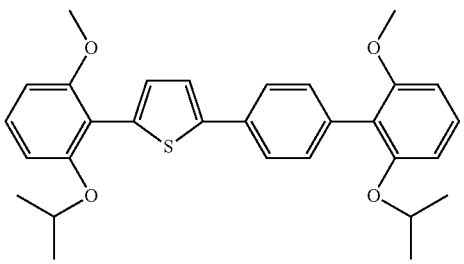

B-23
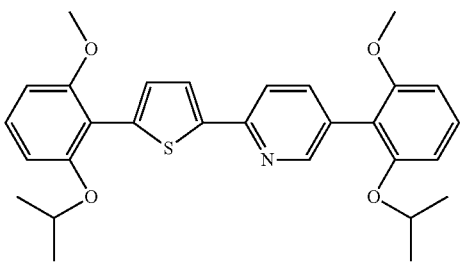

B-24
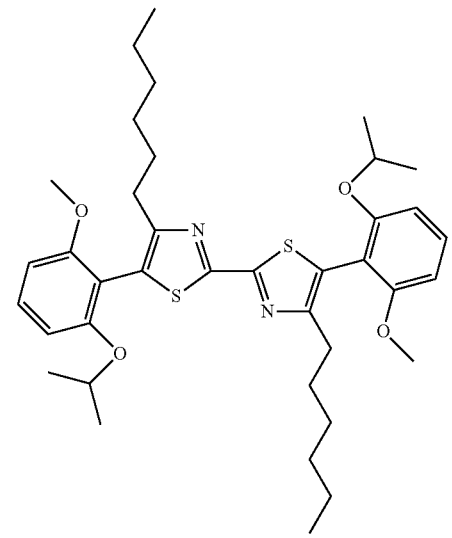

Among these exemplified compounds, the compounds illustrated in group A are examples of a compound including dithienothiophene serving as the electrochromic portion. The compounds illustrated in group B are examples of a compound in which the substituent on the peripheral portion is a methoxy group or an isopropoxy group.

Each of the compounds illustrated in group A and group B has a structure in which the peripheral portion protects the electrochromic portion that exhibits electrochromic properties.

Thus, EC devices containing these compounds serving as EC materials have high durability against the repetition of a redox reaction.

The organic EC compound according to this embodiment may be synthesized from a combination of a halide of a compound to be formed into the electrochromic portion and a boronic acid or boronate of a compound to be formed into the peripheral portion or from a combination of a boronic acid or boronate of a compound to be formed into the electrochromic portion and a halide of a compound to be formed into the peripheral portion, by a coupling reaction in the presence of a Pd catalyst.

An example of a synthesis method for the case where the electrochromic portion is composed of dithienothiophene is illustrated in formula [3]. In the formula, X represents a halogen atom; and A and A' each represent a substituent on the peripheral portion. The dithienothiophene moiety in the formula may be replaced with other organic EC compounds to synthesize the organic EC compounds according to this embodiment.

[Chem. 11]

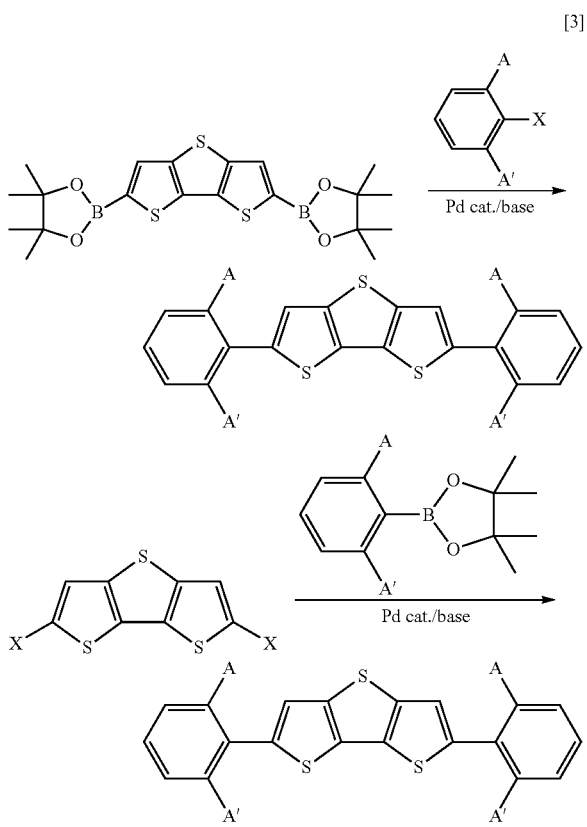

In the external electrode according to this embodiment, the organic EC compound according to this embodiment may be used alone, together with another organic EC compound according to this embodiment, or together with another known organic EC compound.

A first aspect of the EC device according to this embodiment is an EC device including a liquid in which an anodically EC organic compound alone is dissolved in a solvent, the anodically EC organic compound being colored by oxidation. A second aspect thereof is an EC device including a liquid in which an anodically EC organic compound and a cathodically EC organic compound, such as viologen, are both dissolved in a solvent, the cathodically EC organic compound being colored by reduction.

The device having the structure according to the first aspect is referred to as a "unipolar-type device". The device having the structure according to the second aspect is referred to as a "bipolar-type device".

In the case where the bipolar-type device is driven, radical cations are formed by an oxidation reaction on one electrode, and radical cations are formed by reduction on the other electrode.

The radical cations and the radical cations diffuse in the solution and collide with each other to cause a redox reaction. That is, the redox reaction occurs in portions other than the electrodes. Thus, the radical cations and the radical cations disappear. In other words, they are formed into substances before the redox reaction, thereby causing bleaching.

The rate of a coloring reaction needs to be higher than that of the bleaching reaction. Thus, the redox reaction on the electrodes needs to be performed at a higher rate than that of the reaction in the liquid.

For this reason, a large current is required, so that the power consumption is higher than that of the unipolar-type device. From this point of view, the unipolar-type EC device according to the first aspect is preferred.

Next, members constituting the EC device according to this embodiment will be described. First, the electrolyte and the solvent contained in the liquid in the EC device will be described together with the organic EC compound.

The electrolyte is not limited as long as it is an ionically dissociable salt, has satisfactory solubility in a solvent, and high compatibility if it is a solid electrolyte. In particular, the electrolyte preferably has electron-donating properties.

Examples of a supporting electrolyte include inorganic ionic salts, such as various alkali metal salts and alkaline-earth metal salts; quaternary ammonium salts; and cyclic quaternary ammonium salts.

Specific examples thereof include salts of alkali metals of Li, Na, and K, such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, $KSCN$, and $KCl$; and quaternary ammonium salts and cyclic quaternary ammonium salts, such as $(CH_3)_4NBF_4$, $(C_2H_5)_4NBF_4$, $(n\text{-}C_4H_9)_4NBF_4$, $(C_2H_5)_4NBr$, $(C_2H_5)_4NClO_4$, and $(n\text{-}C_4H_9)_4NClO_4$.

The solvent that dissolves the organic EC compound and the supporting electrolyte is not particularly limited as long as it can dissolve the organic EC compound and the supporting electrolyte. In particular, the solvent preferably has polarity.

Specific examples thereof include polar organic solvents, such as methanol, ethanol, propylene carbonate, ethylene carbonate, dimethyl sulfoxide, dimethoxyethane, γ-butyrolactone, γ-valerolactone, sulfolane, dimethylformamide, dimethoxyethane, tetrahydrofuran, acetonitrile, propionitrile, benzonitrile, dimethylacetamide, methylpyrrolidinone, and dioxolane.

Furthermore, a highly viscous or gel-like composition prepared by further incorporating a polymer or a gelling agent into the EC medium may be used.

The polymer is not particularly limited. Examples thereof include polyacrylonitrile, carboxymethyl cellulose, polyvinyl chloride, polyethylene oxide, polypropylene oxide, polyurethane, polyacrylate, polymethacrylate, polyamide, polyacrylamide, polyester, and Nafion (registered trademark).

Next, the transparent substrates and the transparent electrodes will be described. As the transparent substrates 10, for example, colorless or colored glass, tempered glass, or a colorless or colored transparent resin may be used.

Specific examples thereof include polyethylene terephthalate, polyethylene naphthalate, polynorbornene, polyamide, polysulfone, polyether sulfone, polyether ether ketone, polyphenylene sulfide, polycarbonate, polyimide, and polymethyl methacrylate.

Examples of the electrode material 11 include metals and metal oxides, such as indium tin oxide alloys (ITO), fluorine-doped tin oxide (FTC)), tin oxide (NESA), indium zinc oxide (IZO), silver oxide, vanadium oxide, molybdenum oxide, gold, silver, platinum, copper, indium, and chromium; silicon materials, such as polycrystalline silicon and amorphous silicon; and carbon materials, such as carbon black, graphite, glassy carbon.

Furthermore, conductive polymers having improved conductivity by doping treatment and so forth (e.g., polyaniline, polypyrrole, polythiophene, polyacetylene, polyparaphenylene, and complexes of polyethylenedioxythiophene (PEDOT) and polystyrene sulfonic acid) may be preferably used.

In an optical filter according to this embodiment, the optical filter requires transparency. Thus, ITO, FTO, IZO, NESA, conductivity-improved conductive polymers, which do not absorb light in the visible region, are particularly preferably used. A known method for improving conductivity may be employed.

They may be used in various forms, such as bulk and fine-particle forms. These electrode materials may be used alone. Alternatively, the plural electrode materials may be used in combination.

The spacers 13 are arranged between the pair of electrodes 11 to give a space to accommodate the composition 12 containing the organic EC compound. Specifically, polyimide, Teflon, fluorocarbon rubber, epoxy resins, and so forth may be used. The spacers are able to maintain the interelectrode distance of the EC device.

The EC device according to this embodiment may include an inlet for liquid, the inlet being formed by the pair of electrodes and the spacers. After the composition containing the organic EC compound is fed from the inlet, the inlet is covered with a sealing member. Then the inlet is hermetically sealed with an adhesive or the like, thereby providing a device.

The sealing member also serves to ensure isolation such that the adhesive does not come into contact with the organic EC compound. While the shape of the sealing member is not particularly limited, a tapered shape, such as a wedge shape, is preferred.

The EC device according to this embodiment preferably has an interelectrode distance of 150 μm or less. The reason for this is that because the peripheral portion of the organic EC compound according to this embodiment has a large excluded volume, the diffusion velocity in the solution is low.

In the device having a low diffusion velocity of the organic EC compound, it takes a long time from the time of the application of a voltage to the device until the transmittance of the device reaches a target transmittance. That is, the device is one having a low response speed. For the compound having low diffusion velocity, a reduction in diffusion length increases the response speed. In the EC device, a reduction in interelectrode distance results in a reduction in diffusion length.

The EC device according to this embodiment has characteristics in which the bleaching response speed is sharply changed at an interelectrode distance of about 150 μm, as described in Example 10.

The response speed of the EC device is preferably 10 seconds or less. The response speed of the EC device according to this embodiment is 10 seconds or less when the interelectrode distance is 150 μm or less.

The EC device according to this embodiment having an interelectrode distance of 150 μm or less has a high response speed.

The lower limit of the interelectrode distance is 100 nm in order to inhibit the electrical continuity between the electrodes. That is, the interelectrode distance of the EC device according to this embodiment is preferably in the range of 100 nm to 150 μm.

The term "response time" used in this embodiment indicates the length of time from a state having the initial transmittance until the state is changed to a state having a transmittance of 95%.

A method for forming the EC device according to this embodiment is not particularly limited. A method may be employed in which an organic EC compound-containing liquid prepared in advance is injected into a gap between the pair of electrode substrates by, for example, a vacuum injection method, an atmospheric injection method, or a meniscus method.

The EC device according to this embodiment may be used for optical filters, lens units, and image pickup apparatuses.

The EC device according to this embodiment has high durability, high transmittance in a bleached state, and a high coloring-bleaching response speed and thus may be preferably used to control the quantity of light incident on an image pickup device in a camera or the like and to control the properties of the incident wavelength distribution. The control of the incident wavelength distribution is effective in converting the color temperature.

That is, the arrangement of the EC device in an optical path of an image pickup optical system communicating with the image pickup device enables us to control the quantity of light incident on the image pickup device or the properties of the incident wavelength distribution. The image pickup optical system may also be referred to as a lens system. Examples of the image pickup optical system include lens units each including a plurality of lenses.

The EC device according to this embodiment functions as an optical filter when connected to a transistor. Examples of the transistor include TFT and MIM devices.

An image pickup apparatus according to this embodiment includes an image pickup device and an image pickup optical system including an optical filter. The EC device included in the image pickup apparatus may be located at any position, e.g., a position in front of the image pickup optical system or a position right in front of the image pickup device.

The EC device provides high transmittance in a bleached state. Thus, a sufficient quantity of light transmitted is provided with respect to incident light. Furthermore, in a colored state, optical properties in which incident light is surely shielded or modulated are provided. Moreover, the EC device has excellent redox cycle properties and thus has a long lifetime.

EXAMPLES

Examples of a method for synthesizing an organic EC compound according to this embodiment will be described below. Target organic EC compounds may be synthesized by appropriately changing electrochromic portions and peripheral portions in synthesis examples.

Synthesis Example 1

Synthesis of Exemplified Compound A-1

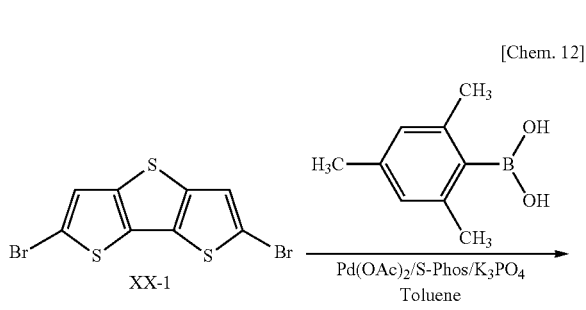

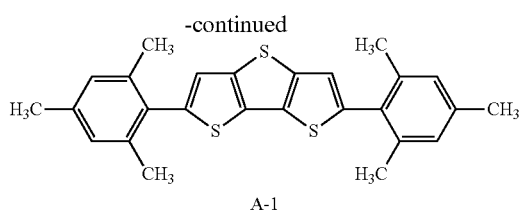

A-1

In a 50-mL reaction vessel, XX-1 (2,6-dibromodithieno[3,2-b:2',3'-d]thiophene) (732 mg, 2.06 mmol) and 2,4,6-trimethylphenylboronic acid (994 mg, 6.06 mmol) were dissolved in toluene (6 ml). Dissolved oxygen was removed by nitrogen.

Next, Pd(OAc)$_2$ (7.1 mg, 0.0316 mmol), 2-dicyclohexylphosphino-2',6'-dimethoxybiphenyl (S-Phos) (32.4 mg, 0.0792 mmol), and tripotassium phosphate (1.68 g, 7.92 mmol) were added thereto in a nitrogen atmosphere. The mixture was heated and refluxed at 130° C. to perform a reaction for 12 hours.

The reaction solution was cooled to room temperature and then concentrated under reduced pressure. Separation and purification were performed by silica-gel chromatography (mobile phase: hexane) to give a white solid power A-1 (510 mg, yield: 57%). Measurement by matrix-assisted laser desorption ionization-mass spectrometry (MALDl-MS) demonstrated that M+ of this compound was found to be 433.

Synthesis Example 2

Synthesis of Exemplified Compound A-7

In a 50-ml reaction vessel, XX-2 (526.2 mg, 1.17 mmol) and XX-3 (1071.2 mg, 3.0 mmol) were mixed in a toluene/ethyl alcohol/tetrahydrofuran (6 ml/3 ml/8 ml) mixed solvent. Dissolved oxygen was removed by nitrogen.

Note that XX-3 is a compound synthesized according to The Journal of Organic Chemistry, 51, 3162 (1986).

Next, Pd(PPh$_3$)$_4$ (14.0 mg, 0.01215 mmol) and an aqueous solution (1.5 ml) of 2 M cesium carbonate were added thereto in a nitrogen atmosphere. The mixture was then heated at 85° C. to perform a reaction for 12 hours.

The reaction solution was cooled to room temperature and then concentrated under reduced pressure. Separation and purification were performed by silica-gel chromatography (mobile phase: hexane/chloroform=3/2) to give a white solid power A-7 (72 mg, yield: 9.4%). Measurement by MALDl-MS demonstrated that M+ of this compound was found to be 652.

The longest absorption wavelength of XX-3 to be formed into the structure of the peripheral portion was 307 nm. The longest absorption wavelength of dithienothiophene to be formed into the structure of the electrochromic portion was 335 nm. That is, the longest absorption wavelength of the electrochromic portion was longer than that of the peripheral portion.

[Chem. 13]

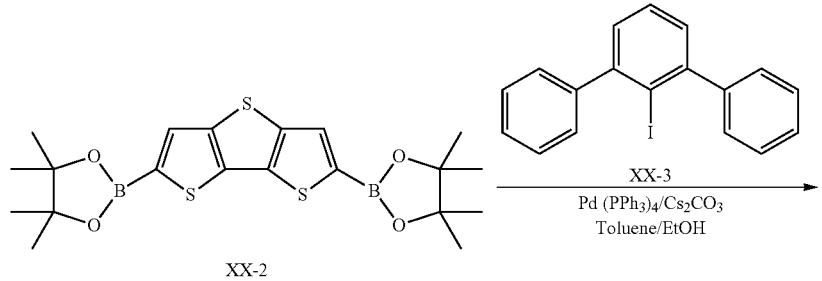

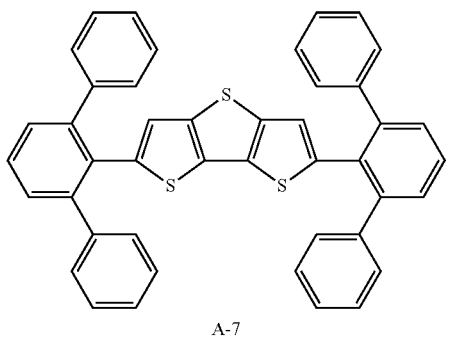

A-7

Synthesis Example 3

Synthesis of Exemplified Compound A-10

[Chem. 14]

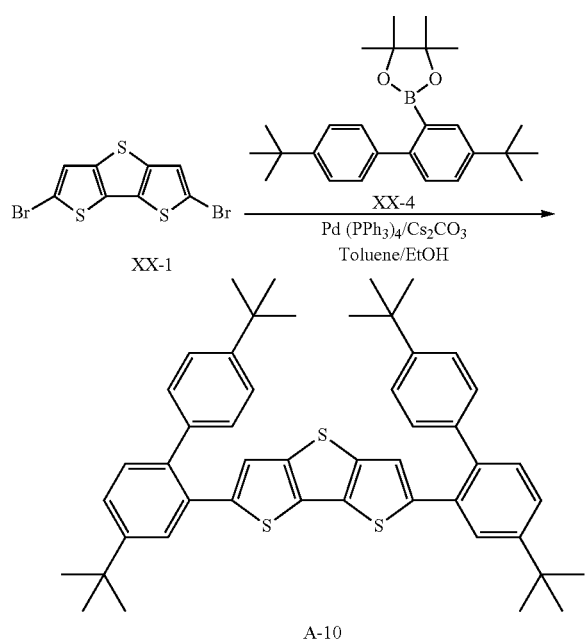

In a 50-ml reaction vessel, XX-1 (177.05 mg, 0.50 mmol) and XX-4 (588.6 mg, 1.50 mmol) were mixed in a toluene/ethyl alcohol (6 ml/2 ml) mixed solvent. Dissolved oxygen was removed by nitrogen.

Note that XX-4 is a compound synthesized according to WO2005/054212. Next, Pd(PPh3)4 (57.8 mg, 0.05 mmol) and an aqueous solution (1.0 ml) of 2 M cesium carbonate were added thereto in a nitrogen atmosphere. The mixture was then heated at 85° C. to perform a reaction for 17 hours.

The reaction solution was cooled to room temperature and then concentrated under reduced pressure. Separation and purification were performed by silica-gel chromatography (mobile phase: hexane/toluene=5/1) to give a white solid power A-10 (125 mg, yield: 29%). Measurement by MALDl-MS demonstrated that M+ of this compound was found to be 724.

Synthesis Example 4

Synthesis of Exemplified Compound A-12

[Chem. 15]

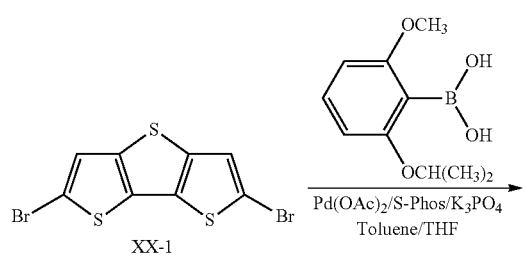

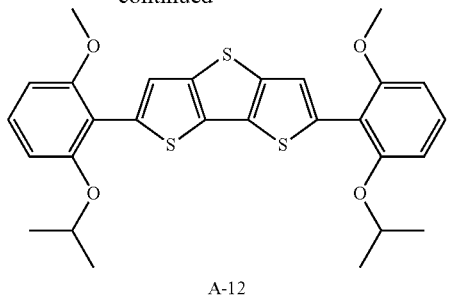

A-12

In a 50-ml reaction vessel, XX-1 (177.05 mg, 0.50 mmol) and 2-isopropoxy-6-methoxyphenylboronic acid (420 mg, 2.0 mmol) were mixed in a toluene/tetrahydrofuran (6 ml/3 ml) mixed solvent. Dissolved oxygen was removed by nitrogen.

Next, Pd(OAc)$_2$ (2.3 mg, 0.01 mmol), 2-dicyclohexylphosphino-2',6'-dimethoxybiphenyl (S-Phos) (10.3 mg, 0.025 mmol), and tripotassium phosphate (575.7 mg, 2.5 mmol) were added thereto in a nitrogen atmosphere. The mixture was then heated at 110° C. to perform a reaction for 8 hours.

The reaction solution was cooled to room temperature and then concentrated under reduced pressure. Separation and purification were performed by silica-gel chromatography (mobile phase: hexane/chloroform=1/2) to give a white solid power A-12 (187 mg, yield: 71%). Measurement by MALDl-MS demonstrated that M+ of this compound was found to be 524.

Synthesis Example 5

Synthesis of Exemplified Compound B-1

[Chem. 16]

B-1

In a 50-ml reaction vessel, XX-5 (2,5-dibromothiophene) (241.9 mg, 1.0 mmol) and 2-isopropoxy-6-methoxyphenyl-boronic acid (753.1 mg, 3.5 mmol) were mixed in a toluene/tetrahydrofuran (4 ml/4 ml) mixed solvent. Dissolved oxygen was removed by nitrogen.

Next, Pd(OAc)$_2$ (4.5 mg, 0.02 mmol), 2-dicyclohexylphosphino-2',6'-dimethoxybiphenyl (S-Phos) (20.53 mg, 0.05 mmol), and tripotassium phosphate (1162.4 mg, 5.05 mmol) were added thereto in a nitrogen atmosphere. The mixture was then heated at 110° C. to perform a reaction for 8 hours.

The reaction solution was cooled to room temperature and then concentrated under reduced pressure. Separation and purification were performed by silica-gel chromatography (mobile phase: hexane/chloroform=1/4) to give a white solid power B-1 (362.8 mg, yield: 86.3%). Measurement by MALDl-MS demonstrated that M+ of this compound was found to be 412.2.

Synthesis Example 6

Synthesis of Exemplified Compound B-6

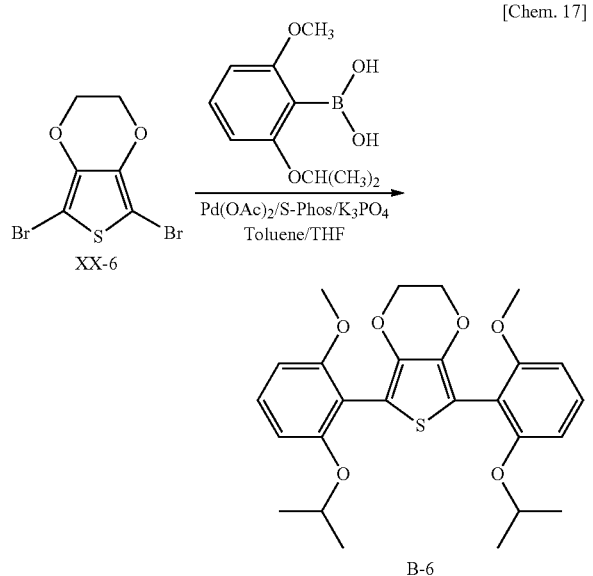

[Chem. 17]

In a 50-ml reaction vessel, XX-6 (2,5-dibromoethylenedioxythiophene) (500 mg, 1.67 mmol) and 2-isopropoxy-6-methoxyphenylboronic acid (1.05 g, 5.0 mmol) were mixed in a toluene/tetrahydrofuran (10 ml/5 ml) mixed solvent. Dissolved oxygen was removed by nitrogen.

Next, Pd(OAc)$_2$ (19 mg, 0.083 mmol), 2-dicyclohexylphosphino-2',6'-dimethoxybiphenyl (S-Phos) (89 mg, 0.22 mmol), and tripotassium phosphate (1.92 g, 8.35 mmol) were added thereto in a nitrogen atmosphere. The mixture was then heated and refluxed at 110° C. to perform a reaction for 7 hours.

The reaction solution was cooled to room temperature and then concentrated under reduced pressure. Separation and purification were performed by silica-gel chromatography (mobile phase: hexane/ethyl acetate=4/3) to give a white solid power B-6 (420 mg, yield: 54%). Measurement by MALDl-MS demonstrated that M+ of this compound was found to be 470.

Synthesis Example 7

Synthesis of Exemplified Compound B-7

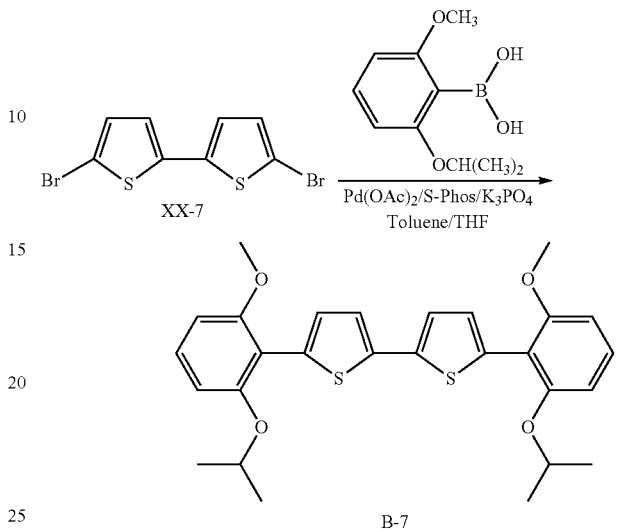

[Chem. 18]

In a 50-ml reaction vessel, XX-7 (2,5-dibromobithiophene) (326.3 mg, 1.01 mmol) and 2-isopropoxy-6-methoxyphenylboronic acid (749.8 mg, 3.57 mmol) were mixed in a toluene/tetrahydrofuran (4 ml/4 ml) mixed solvent. Dissolved oxygen was removed by nitrogen.

Next, Pd(OAc)$_2$ (5.9 mg, 0.026 mmol), 2-dicyclohexylphosphino-2',6'-dimethoxybiphenyl (S-Phos) (21.4 mg, 0.052 mmol), and tripotassium phosphate (1123.7 mg, 4.88 mmol) were added thereto in a nitrogen atmosphere. The mixture was then heated and refluxed at 110° C. to perform a reaction for 8 hours.

The reaction solution was cooled to room temperature and then concentrated under reduced pressure. Separation and purification were performed by silica-gel chromatography (mobile phase: hexane/chloroform=1/3) to give a white solid power B-7 (418.8 mg, yield: 84.1%). Measurement by MALDl-MS demonstrated that M+ of this compound was found to be 494.2.

Synthesis Example 8

Synthesis of Exemplified Compound B-10

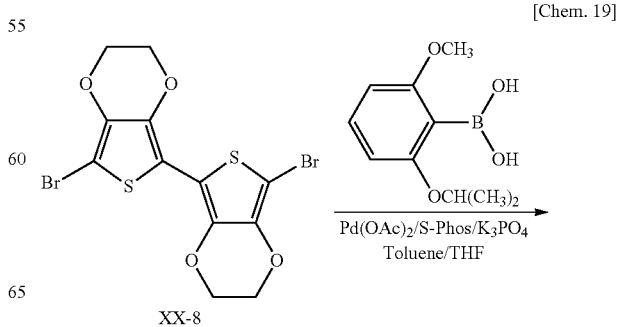

[Chem. 19]

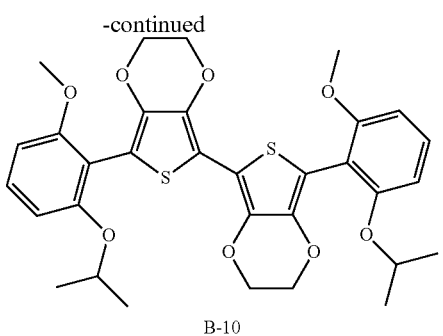

B-10

In a 50-ml reaction vessel, XX-8 (440.1 mg, 1 mmol) and 2-isopropoxy-6-methoxyphenylboronic acid (751.1 mg, 3.58 mmol) were mixed in a toluene/tetrahydrofuran (4 ml/4 ml) mixed solvent. Dissolved oxygen was removed by nitrogen.

Next, Pd(OAc)$_2$ (5.1 mg, 0.023 mmol), 2-dicyclohexylphosphino-2',6'-dimethoxybiphenyl (S-Phos) (22.8 mg, 0.056 mmol), and tripotassium phosphate (1193.1 mg, 5.18 mmol) were added thereto in a nitrogen atmosphere. The mixture was then heated and refluxed at 110° C. to perform a reaction for 8 hours.

The reaction solution was cooled to room temperature and then concentrated under reduced pressure. Separation and purification were performed by silica-gel chromatography (mobile phase: hexane/ethyl acetate=4/3) to give a white solid power B-10 (177.3 mg, yield: 29.03%). Measurement by MALDl-MS demonstrated that M+ of this compound was found to be 610.2.

Synthesis Example 9

Synthesis of Exemplified Compound B-11

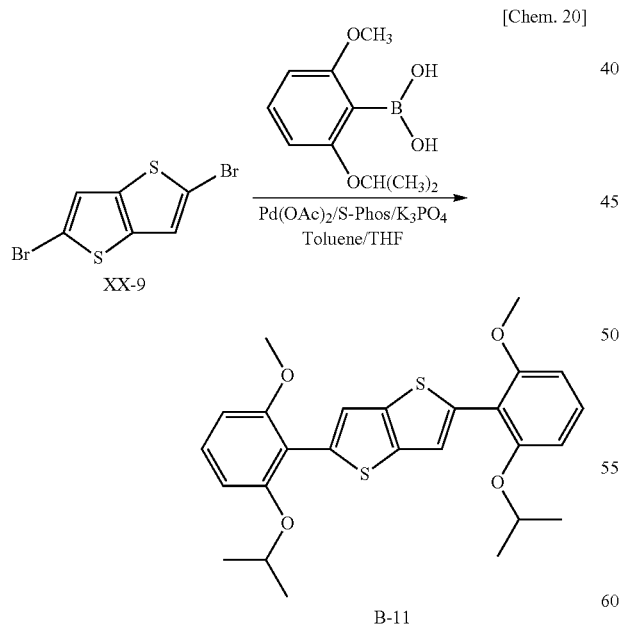

[Chem. 20]

B-11

In a 50-ml reaction vessel, XX-9 (200 mg, 0.671 mmol) and 2-isopropoxy-6-methoxyphenylboronic acid (563 mg, 2.684 mmol) were mixed in a toluene/tetrahydrofuran (6 ml/3 ml) mixed solvent. Dissolved oxygen was removed by nitrogen.

Next, Pd(OAc)$_2$ (3.0 mg, 0.013 mmol), 2-dicyclohexylphosphino-2',6'-dimethoxybiphenyl (S-Phos) (13.8 mg, 0.034 mmol), and tripotassium phosphate (772 mg, 3.36 mmol) were added thereto in a nitrogen atmosphere. The mixture was then heated and refluxed at 110° C. to perform a reaction for 8 hours.

The reaction solution was cooled to room temperature and then concentrated under reduced pressure. Separation and purification were performed by silica-gel chromatography (mobile phase: hexane/chloroform=1/2) to give a white solid power B-11 (235 mg, yield: 75%). Measurement by MALDl-MS demonstrated that M+ of this compound was found to be 468.

Synthesis Example 10

Synthesis of Exemplified Compound B-16

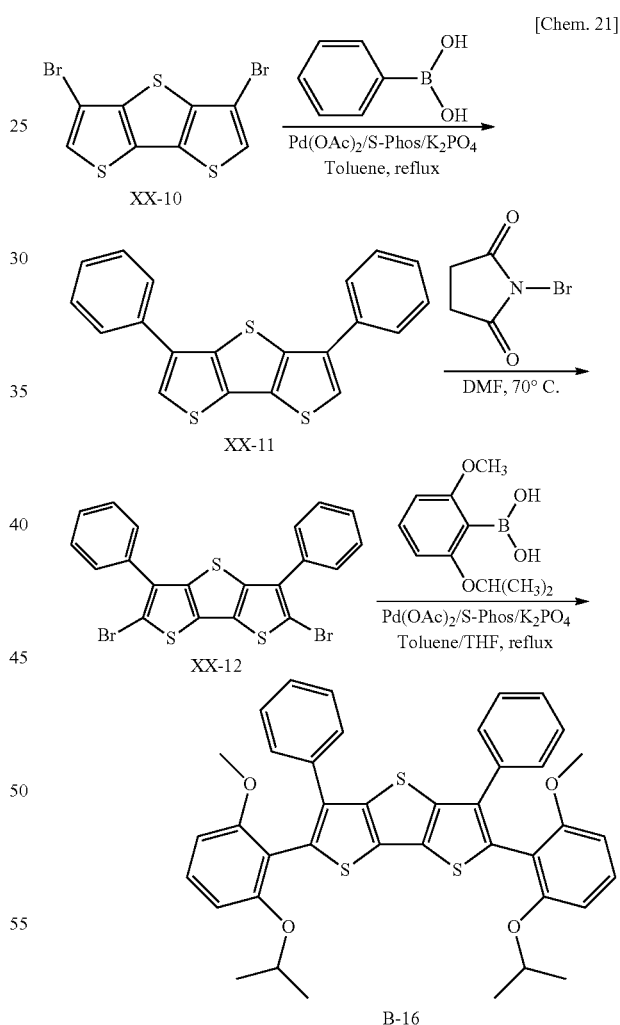

[Chem. 21]

B-16

(1) In a 300-mL reaction vessel, XX-10 (1.25 g, 3.53 mmol) and phenylboronic acid (1.29 g, 10.59 mmol) were dissolved in toluene (70 ml). Dissolved oxygen was removed by nitrogen.

Next, Pd(OAc)$_2$ (15.9 mg, 0.0706 mmol), 2-dicyclohexylphosphino-2',6'-dimethoxybiphenyl (S-Phos) (72.5 mg, 0.1765 mmol), and tripotassium phosphate (3.75 g, 17.65 mmol) were added thereto in a nitrogen atmosphere. The mixture was then heated and refluxed at 140° C. to perform a reaction for 13 hours.

The reaction solution was cooled to room temperature and then concentrated under reduced pressure. Separation and purification were performed by silica-gel chromatography (mobile phase: hexane/ethyl acetate) to give a white solid power XX-11 (1.23 g, yield: 100%).

(2) In a 300-mL reaction vessel, XX-11 (1.13 g, 3.242 mmol) obtained in item (1) was dissolved in N,N-dimethylformamide (DMF) (65 ml). Then N-bromosuccinimide (1.44 g, 8.106 mmol) was added thereto. The mixture was stirred at 70° C. for 24 hours. The reaction solution was cooled to room temperature. Then the reaction solution was subjected to extraction with chloroform, washing with water, and concentration under reduced pressure to give a pale yellow power XX-12 (1.55 g, yield: 94%).

(3) In a 50-ml reaction vessel, XX-12 (200 mg, 0.395 mmol) and 2-isopropoxy-6-methoxyphenylboronic acid (332 mg, 1.580 mmol) were mixed in a toluene/tetrahydrofuran (3 ml/3 ml) mixed solvent. Dissolved oxygen was removed by nitrogen. Next, Pd(OAc)$_2$ (1.8 mg, 0.0079 mmol), 2-dicyclohexylphosphino-2',6'-dimethoxybiphenyl (S-Phos) (8.13 mg, 0.0198 mmol), and tripotassium phosphate (455 mg, 1.98 mmol) were added thereto in a nitrogen atmosphere. The mixture was then heated and refluxed to perform a reaction for 8 hours.

The reaction solution was cooled to room temperature and then concentrated under reduced pressure. Separation and purification were performed by silica-gel chromatography (mobile phase: hexane/chloroform=1/2) to give a white solid power B-16 (225 mg, yield: 84%). Measurement by MALDl-MS demonstrated that M$^+$ of this compound was found to be 676.

Synthesis Example 11

Synthesis of Exemplified Compound B-18

[Chem. 22]

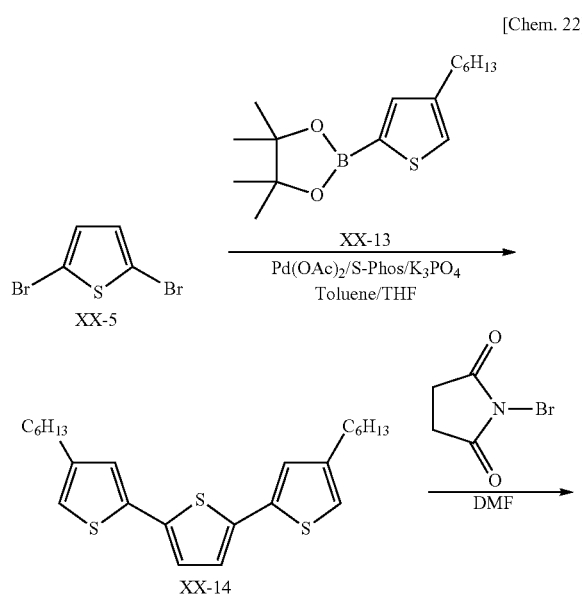

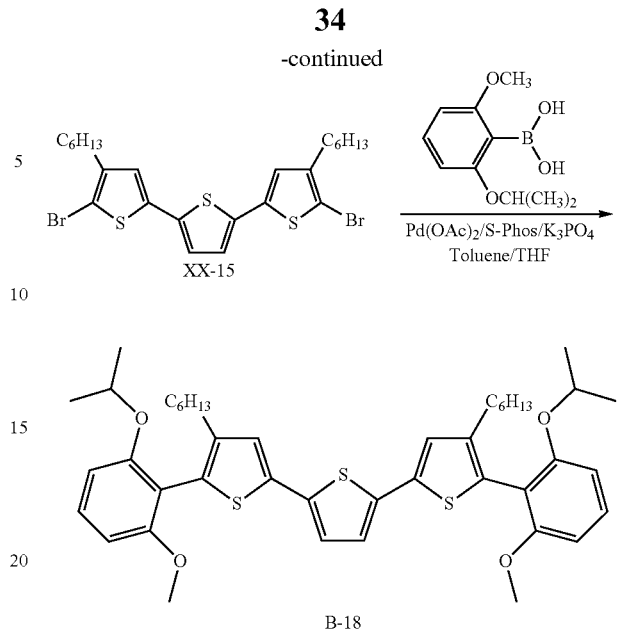

(1) In a 50-ml reaction vessel, XX-5 (300 mg, 1.24 mmol) and XX-13 (1.10 g, 3.72 mmol) were mixed in a toluene/tetrahydrofuran (8 ml/4 ml) mixed solvent. Dissolved oxygen was removed by nitrogen.

Next, Pd(OAc)$_2$ (8.4 mg, 0.037 mmol), 2-dicyclohexylphosphino-2',6'-dimethoxybiphenyl (S-Phos) (40.7 mg, 0.0992 mmol), and tripotassium phosphate (1.43 g, 6.2 mmol) were added thereto in a nitrogen atmosphere. The mixture was then heated and refluxed at 110° C. to perform a reaction for 7 hours.

The reaction solution was cooled to room temperature and then concentrated under reduced pressure. Separation and purification were performed by silica-gel chromatography (mobile phase: hexane) to give a colorless viscous liquid XX-14 (360 mg, yield: 70%).

(2) In a 100-mL reaction vessel, XX-14 (355 mg, 0.852 mmol) obtained in item (1) was dissolved in N,N-dimethylformamide (DMF) (25 ml).

Then N-bromosuccinimide (333 mg, 1.87 mmol) was added thereto. The mixture was stirred at room temperature for 8 hours. Water was added to the reaction solution. Then the reaction solution was subjected to extraction with chloroform, washing with water, and concentration under reduced pressure to give XX-15 (470 mg, yield: 96%).

(3) In a 50-ml reaction vessel, XX-15 (470 mg, 0.818 mmol) and 2-isopropoxy-6-methoxyphenylboronic acid (515 mg, 2.45 mmol) were mixed in a toluene/tetrahydrofuran (5 ml/2.5 ml) mixed solvent. Dissolved oxygen was removed by nitrogen.

Next, Pd(OAc)$_2$ (5.5 mg, 0.0245 mmol), 2-dicyclohexylphosphino-2',6'-dimethoxybiphenyl (S-Phos) (27 mg, 0.065 mmol), and tripotassium phosphate (942 mg, 4.09 mmol) were added thereto in a nitrogen atmosphere. The mixture was then heated and refluxed to perform a reaction for 7 hours.

The reaction solution was cooled to room temperature and then concentrated under reduced pressure. Separation and purification were performed by silica-gel chromatography (mobile phase: hexane/chloroform=1/2) to give a pale yellow solid B-18 (520 mg, yield: 85%). Measurement by MALDI-MS demonstrated that M+ of this compound was found to be 744.

Synthesis Example 12

Synthesis of Exemplified Compound B-24

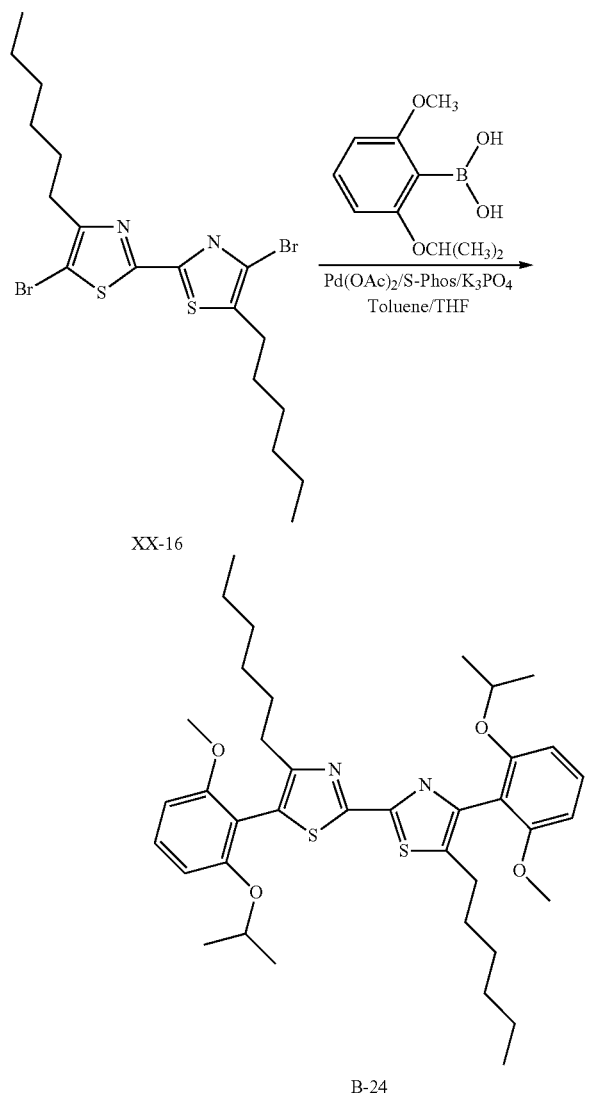

[Chem. 23]

B-24

In a 50-ml reaction vessel, XX-16 (559.5 mg, 1.13 mmol) and 2-isopropoxy-6-methoxyphenylboronic acid (771.0 mg, 3.67 mmol) were mixed in a toluene/tetrahydrofuran (6 ml/4 ml) mixed solvent. Dissolved oxygen was removed by nitrogen.

Next, Pd(OAc)$_2$ (6.7 mg, 0.03 mmol), 2-dicyclohexylphosphino-2',6'-dimethoxybiphenyl (S-Phos) (21.3 mg, 0.052 mmol), and tripotassium phosphate (1166.2 mg, 5.06 mmol) were added thereto in a nitrogen atmosphere. The mixture was then heated and refluxed at 110° C. to perform a reaction for 8 hours.

The reaction solution was cooled to room temperature and then concentrated under reduced pressure. Separation and purification were performed by silica-gel chromatography (mobile phase: hexane/ethyl acetate=4/1) to give a white solid power B-24 (545.8 mg, yield: 72.5%). Measurement by MALDI-MS demonstrated that M+ of this compound was found to be 664.

Example 1

Electrochromic Properties

Each of the compounds described in the synthesis examples was dissolved in chloroform. The absorption spectrum of each solution in a neutral state (bleached state) was measured with an ultraviolet and visible spectrophotometer (V-560, manufactured by JASCO Corporation).

Measurement of the absorption spectrum at the time of oxidation (colored) was performed as follows: a liquid in which the compound described in the synthesis example was dissolved ($5.0 \times 10^{-4}$ mol/L) in a dichloromethane solution of 0.1 mol/L tetrabutylammonium perchlorate, serving as a supporting electrolyte, was subjected to constant potential oxidation at a potential equal to or higher than the oxidation potential of the compound using a working electrode composed of platinum, a counter electrode composed of platinum, and a reference electrode composed of silver, thereby measuring the absorption spectrum and the transmittance spectrum changes.

Table 3 illustrates the results.

TABLE 3

| Compound No. | Bleached state λ max (nm) | Colored state λ max (nm) |
|---|---|---|
| A-1 | 308.0 | 433.0 |
| A-7 | 355.0 | 480.0 |
| A-10 | 358.5 | 527.5 |
| A-12 | 364.5 | 566.0 |
| B-1 | 321.0 | 505.0 |
| B-6 | 290.0 | 448.5 |
| B-7 | 371.0 | 617.0 |
| B-10 | 361.0 | 545.0 |
| B-11 | 340.0 | 540.0 |
| B-16 | 307.5 | 513.5 |
| B-18 | 386.0 | 649.0 |
| B-24 | 358.0 | 405.0 |

In any compound, in the neutral state, λmax, at which the absorption peak has the maximum intensity, is in the ultraviolet region. There is no absorption in the entire visible region. Thus, these compounds are transparent.

Furthermore, any colored species formed by oxidation exhibited λmax in the visible region and was visually identified as being colored. The colored state due to oxidation was returned to a colorless transparent state. Thus, electrochromic properties associated with oxidation and reduction were confirmed.

Example 2 and Comparative Example 1

Durable Stability of Organic EC Compound Against Redox Cycles-1

The durable stability of organic EC compounds A-1, A-7, and A-10 according to the present invention and known compound Ref-1 as Comparative Example 1 against redox cycles was evaluated. The structural formula of Ref-1 is illustrated below.

[Chem. 24]

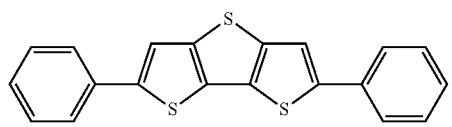

Ref-1

Compound Ref-1 according to Comparative Example 1 is synthesized according to NPL 1 and is a compound that has substantially no function of forming the steric hindrance of the peripheral portion to the electrochromic portion because each of the atoms of the peripheral portion and adjacent to the atom bonded to the electrochromic portion has a hydrogen atom.

The electrochromic portion of this compound is composed of dithienothiophene, and a phenyl group serves as the aromatic ring.

Measurement of the durable stability against the redox cycles was performed as follows: A liquid in which each compound was dissolved ($1.0 \times 10^{-4}$ mol/L) in a dichloromethane solution of 0.1 mol/L tetrabutylammonium perchlorate, serving as a supporting electrolyte, was measured using a working electrode composed of glassy carbon, a counter electrode composed of platinum, and a reference electrode composed of silver.

Figure 2:
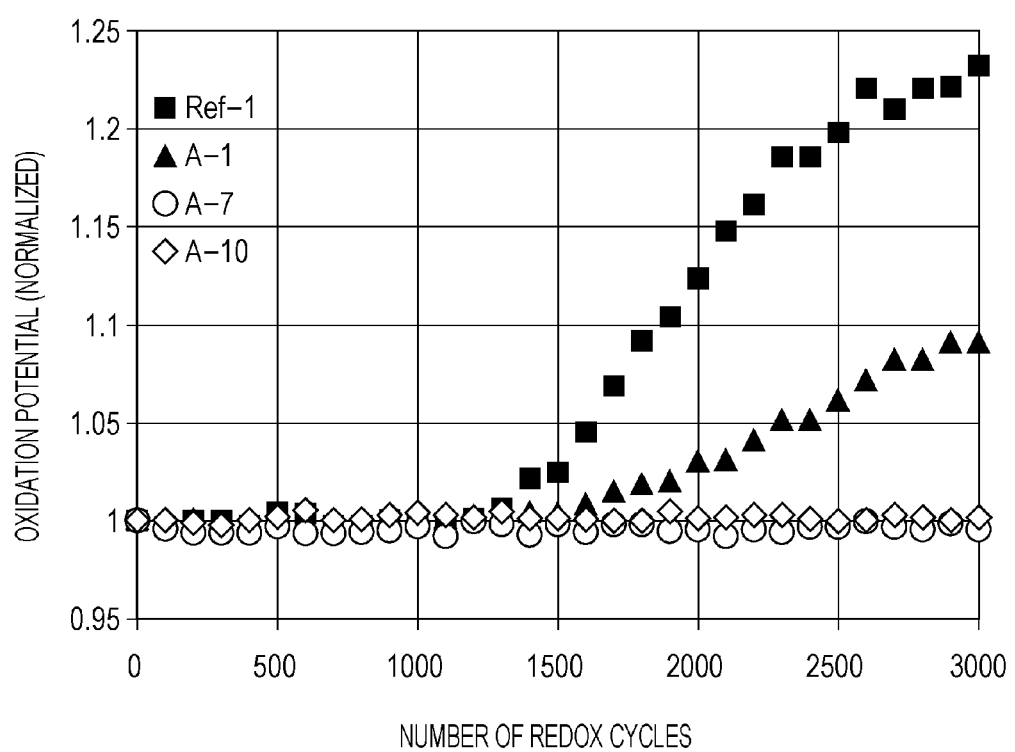
FIG. 2 is a graph illustrating durable stability against redox cycles in Example 2.

A rectangular-wave potential program was repeatedly applied to the solution, the rectangular-wave potential program including constant potential oxidation at a potential equal to or higher than the oxidation potential of the compound for 10 seconds and constant potential reduction at 0 V (vs. Ag/Ag$^+$) for 10 seconds. Cyclic voltammetry (CV) measurement was performed at every 100 redox cycles. FIG. 2 illustrates a change in oxidation potential associated with the number of redox cycles.

In compound Ref-1 according to Comparative Example 1, the oxidation potential started to shift to higher potentials after about 1400 redox cycles. After 3000 cycles, the oxidation potential was increased to about 1.25 times, which indicated the degradation of the compound.

In contrast, for compounds A-7 and A-10 according to the present invention, substantially no change in oxidation potential was observed even after 3000 redox cycles.

Thus, A-7 and A-10 have high durability, compared with Ref-1. This is probably because in the compounds according to the present invention, the substituents on the aromatic ring protect the electrochromic portion. That is, other organic EC compounds according to this embodiment also have high durability.

With respect to the durable stability of compound A-1, the amount of the change in oxidation potential was intermediate between Ref-1 and either A-7 or A-10. The methyl groups on the aromatic rings each have a relatively weak function of forming steric hindrance. Thus, the excluded volume effect is provided to some extent, compared with Ref-1.

Example 3 and Comparative Example 2

Durable Stability of Organic EC Compound Against Redox Cycles-2

The durable stability of organic EC organic compounds A-7, A-10, A-12, B-1, B-6, B-10, B-16, and B-18 according to this embodiment and known compounds Ref-1, Ref-2, and Ref-3 as Comparative Example 2 against redox cycles was evaluated. The structural formulae of Ref-2 and Ref-3 are illustrated below.

[Chem. 25]

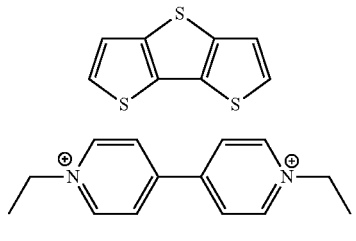

Ref-2

Ref-3

2ClO$_4^-$

Compound Ref-2 according to the comparative example is a compound without a peripheral portion. Compound Ref-3 is a known organic EC compound (diethylviologen diperchlorate) that is colored by reduction.

In this example, measurement of the durable stability against the redox cycles was performed as follows: A solution and a measuring system the same as those in Example 2 were used. A rectangular-wave potential program was repeated 20,000 cycles, the rectangular-wave potential program including constant potential oxidation at a potential equal to or higher than the oxidation potential of the compound for 10 seconds and constant potential reduction at 0 V (vs. Ag/Ag$^+$) for 10 seconds.

Cyclic voltammetry (CV) measurement was performed at every 100 redox cycles. The number of redox cycles at the time of a 20% or more change in oxidation peak current was defined as the number of durable redox cycles. Note that the number of durable redox cycles of a compound in which a change in current after 20,000 cycles was within 20% was defined as 20,000 cycles.

Figure 3:
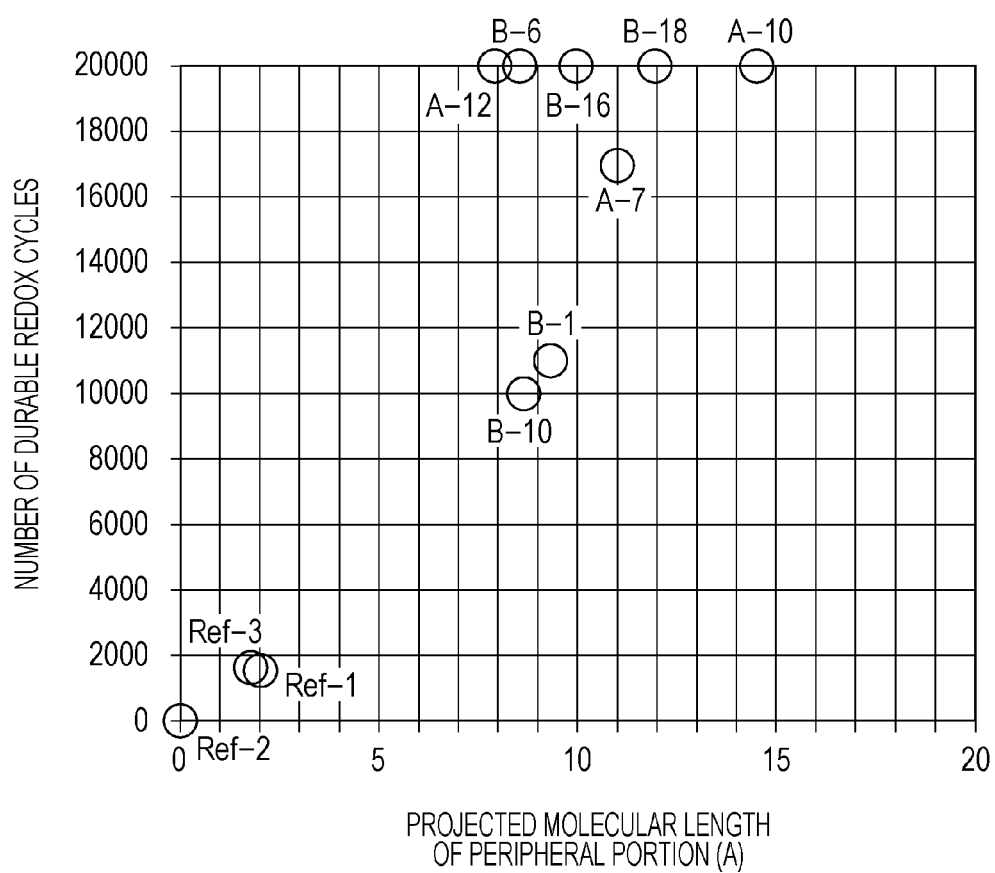
FIG. 3 is a graph illustrating durable stability against redox cycles in Example 3.

FIG. 3 is a graph illustrating the number of durable redox cycles plotted against the projected molecular length of the peripheral portion.

Here, the projected molecular length of the peripheral portion indicates the projected molecular length of a molecular structure determined by structural optimization calculations in a ground state using the electronic state calculation software, Gaussian 03* Revision D. 01, and serves as an indicator of the function of forming steric hindrance against the conjugated plane of the electrochromic portion.

Compound Ref-2 according to the comparative example was subjected to electrolytic polymerization immediately after the application of a voltage and thus did not have redox stability as a compound.

For compounds Ref-1 and Ref-3 that lack the function of protecting the electrochromic portion, the function being provided by the substituent on the peripheral portion, the numbers of durable cycles of Ref-1 and Ref-3 were 1500 and 1600 cycles, respectively, which were low in durable redox stability.

In contrast, in the case of any of the organic EC compounds according to this embodiment, the durable redox stability exhibited 10,000 cycles or more even when the electrochromic portion had various chemical structures.

In the organic EC compound according to this embodiment, the projected molecular length of the substituent on the peripheral portion is 7 Å or more. The electrochromic portion is sterically protected by the effect of a large excluded volume of the substituent on the peripheral portion.

Example 4

Production of EC Device

Lithium perchlorate serving as a supporting electrolyte was dissolved in propylene carbonate in a concentration of 0.1 M. Then B-7, which is an organic EC compound according to the present invention, was dissolved therein in a concentration of 20.0 mM, thereby preparing an EC medium.

An insulating layer ($SiO_2$) was formed on the peripheral part of a glass substrate (lower electrode) provided with a transparent conductive film (ITO) while an opening that defines a coloring-bleaching region was left. A PET film (Melinex S (registered trademark), manufactured by Teijin DuPont Films Japan Limited) that defines a distance between substrates was held by a glass substrate (upper electrode) provided with a transparent conductive film. The peripheral part of the device was sealed with an epoxy-based adhesive while an opening for injecting the EC medium was left, thereby producing an empty cell provided with the inlet.

The thickness of the film was used as the distance between the pair of electrodes of the device according to the present invention. Empty cells having different interelectrode distances were produced using films having different thicknesses.

Next, the foregoing EC medium was injected from the opening of the device by a vacuum injection method. The opening was sealed with the epoxy-based adhesive in the same way as the peripheral part, thereby producing an EC device.

The device according to this example has a device structure (unipolar-type device) in which the anodically EC organic compound is colored on one electrode by oxidation.

<EC Properties of Unipolar-Type Device>

Electrochromic properties of the device having an interelectrode distance of 60 μm were evaluated. This EC device immediately after the production had a transmittance of 80% or more throughout the visible range and thus had high transmittance.

When a voltage of 2.2 V was applied to the device, the device exhibited absorption (506 nm) originating from the oxidized species of compound B-7 and was colored. At the absorption wavelength (506 nm), the coloration efficiency was 473 $cm^2/C$. Furthermore, the device was bleached by the application of a voltage of −0.5 V and exhibited reversible coloring-bleaching behavior.

Example 5

EC Properties of Unipolar-Type Device

A device was produced as in Example 4, except that 5.0 mM of B-24, which is an anodically EC organic compound, was used as the organic EC compound in the EC medium and that FTO was used as the electrode substrates. The resulting unipolar-type device had an interelectrode distance of 70 μm.

When a voltage of 3.4 V was applied to the device, the device exhibited absorption (388 nm) originating from the oxidized species of compound B-24. At the absorption wavelength (388 nm), the coloration efficiency was 1041 $cm^2/C$.

Example 6

EC Properties of Bipolar-Type Device

A device was produced as in Example 4, except that 30.0 mM of B-7, which is an anodically EC organic compound, and 30.0 mM of Ref-3, which is a cathodically EC organic compound, were used as the organic EC compound in the EC medium, tetrabutylammonium perchlorate (0.1 M) was used as the supporting electrolyte, and that FTO was used as the electrode substrates.

The device according to this example has a device structure (bipolar-type device) in which the anodically EC organic compound is colored on one electrode by oxidation and the cathodically EC organic compound is colored on the counter electrode by reduction.

Electrochromic properties of the device having an interelectrode distance of 60 μm were evaluated. This EC device immediately after the production had a transmittance of 80% or more throughout the visible range and thus had high transmittance.

When a voltage of 1.4 V was applied to the device, the device exhibited absorption (506 nm) originating from the oxidized species of compound B-7 and absorption (604 nm) originating from the reduced species of compound Ref-3, and was colored. At the absorption wavelength (506 nm) originating from the oxidized species of the anodically EC organic compound, the coloration efficiency was 470 $cm^2/C$. Furthermore, the device was bleached by the application of a voltage of −0.5 V and exhibited reversible coloring-bleaching behavior.

Example 7

Durable Stability of EC Device Against Redox Cycles

A device was produced as in Example 4, except that 6.0 mM of A-12, which is an anodically EC organic compound, was used as the organic EC compound in the EC medium. The resulting unipolar-type device had an interelectrode distance of 150 μm. When a voltage of 2.3 V was applied to the device, the device exhibited absorption (498 nm) originating from the oxidized species of compound A-12 and was colored.

At the absorption wavelength (498 nm), the coloration efficiency was 1058 $cm^2/C$. Furthermore, the device was bleached by the application of a voltage of −0.5 V and exhibited reversible coloring-bleaching behavior. Next, the durable stability of the EC device against redox cycles was measured.

A triangular wave (electric potential gradient: 200 mV/sec) with peak values of 2.3 V and −0.5 V was repeatedly applied to the EC device according to this example. The EC device exhibited satisfactory coloring-bleaching behavior even after 800 redox cycles.

Example 8

Durable Stability of EC Device against Redox Cycles

A device was produced as in Example 4, except that 6.0 mM of B-16, which is an anodically EC organic compound, was used as the organic EC compound in the EC medium and was dissolved to prepare an EC medium. The resulting unipolar-type device had an interelectrode distance of 150 μm.

When a voltage of 2.6 V was applied to the device, the device exhibited absorption (528 nm) originating from the oxidized species of compound B-16 and was colored.

At the absorption wavelength (528 nm), the coloration efficiency was 240 $cm^2/C$. Furthermore, the device was bleached by the application of a voltage of −0.5 V and exhibited reversible coloring-bleaching behavior.

A triangular wave (electric potential gradient: 200 mV/sec) with peak values of 2.6 V and −0.5 V was repeatedly applied to the EC device according to this example. The EC device exhibited satisfactory coloring-bleaching behavior even after 1000 redox cycles.

Example 9

Durable Stability of EC Device Against Redox Cycles

A device was produced as in Example 4, except that 6.0 mM of A-12, which is an anodically EC organic compound, and 6.0 mM of Ref-3, which is a cathodically EC organic compound, were used as the organic EC compound in the EC medium. The resulting bipolar-type device had an interelectrode distance of 150 µm.

When a voltage of 1.7 V was applied to the device, the device exhibited absorption (498 nm) originating from the oxidized species of compound A-12 and absorption (604 nm) originating from the reduced species of compound Ref-3, and was colored. Furthermore, the device was bleached by the application of a voltage of −0.5 V and exhibited reversible coloring-bleaching behavior.

A triangular wave (electric potential gradient: 200 mV/sec) with peak values of 1.7 V and −0.5 V was repeatedly applied to the EC device according to this example. The EC device exhibited satisfactory coloring-bleaching behavior even after 1600 redox cycles.

Example 10

Bleaching Response Speed

Bipolar-type devices having three types of interelectrode distances (60 µm, 150 µm, and 350 µm) were produced using the EC medium (anodically EC organic compound: 6.0 mM of A-12/cathodically EC organic compound: 6.0 mM of Ref-3) prepared in Example 9. The response time needed to bleach each device was measured.

The bleaching response time in this example indicates the length of time needed to change the optical density from 0.9 (12.5% of the initial transmittance) to 0.02 (95% of the initial transmittance).

Figure 4:
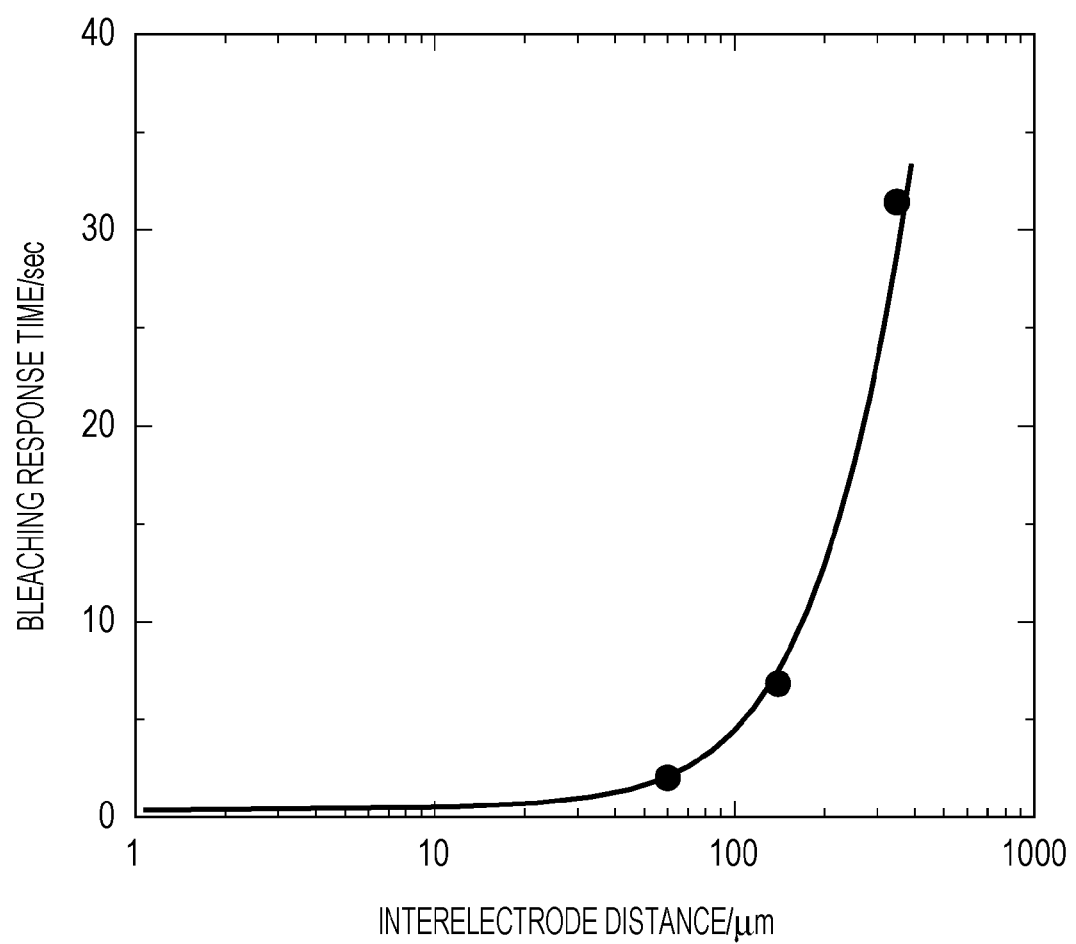
FIG. 4 is a graph illustrating the response time of an EC device in Example 10.

FIG. 4 is a graph illustrating the relationship between the interelectrode distance and the bleaching response speed. At an interelectrode distance of 350 µm, the response time was 31.4 seconds. In contrast, in the case of the device having an interelectrode distance of 150 µm, the response time was 6.8 seconds. In the case of the device having an interelectrode distance of 60 µm, the response time was 2.0 seconds. That is, a reduction in interelectrode distance resulted in significantly satisfactory bleaching response speed.

The solid line in FIG. 4 is a plot of data estimated from the three-point data.

As described above, it is possible to provide the EC device according to the present invention, the EC device having high durable stability against redox cycles, high transparency in the bleached state, i.e., the EC device does not absorb light in the visible region in the bleached state, and having excellent response speed.

The present invention is not limited to the foregoing embodiments. Various changes and modifications may be made without departing from the spirit and scope of the invention. Therefore, the following claims are appended to make public the scope of the invention.

According to the present invention, it is possible to provide an EC device having high durability, a high response speed, and high transparency when the device is bleached.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An electrochromic device comprising a pair of electrodes and a composition arranged between the pair of electrodes, the composition containing an electrolyte and an organic electrochromic compound,
   wherein the organic electrochromic compound includes an electrochromic portion that exhibits electrochromic properties and an aromatic ring directly bonded to the electrochromic portion,
   the electrochromic portion forms one conjugated plane,
   an atom of the aromatic ring and adjacent to an atom bonded to the electrochromic portion has a substituent having a volume equal to or larger than the volume of a methyl group, and
   the pair of electrodes has an interelectrode distance of 150 µm or less.

2. The electrochromic device according to claim 1, wherein the organic electrochromic compound is an anodically electrochromic organic compound.

3. The electrochromic device according to claim 2, wherein the organic electrochromic compound further comprises a cathodically electrochromic organic compound.

4. The electrochromic device according to claim 1, wherein the longest absorption wavelength of the electrochromic portion is longer than the longest absorption wavelength of the aromatic ring.

5. The electrochromic device according to claim 1, wherein the HOMO of the electrochromic portion lies higher than the HOMO of the peripheral portion.

6. The electrochromic device according to claim 1, wherein the electrochromic portion contains a thiophene ring.

7. The electrochromic device according to claim 1, wherein the aromatic ring is a benzene ring.

8. The electrochromic device according to claim 1, wherein the substituent on the aromatic ring is an electron-donating group.

9. The electrochromic device according to claim 8, wherein the electron-donating group on the aromatic ring is an alkoxy group.

10. The electrochromic device according to claim 1, wherein the organic electrochromic compound is an anodically electrochromic organic compound that has absorption in the visible range when oxidized.

11. An optical filter comprising the electrochromic device according to claim 1 and a switching device.

12. A lens unit comprising the optical filter according to claim 11 and an image pickup optical system.

13. An image pickup apparatus comprising an image pickup optical system, the optical filter according to claim 11, and an image pickup device configured to pick up an image through the optical filter.

14. The electrochomic device according to claim 1, wherein the aromatic ring doesn't exhibit electrochromic properties.

* * * * *